US012709773B2

(12) United States Patent
Liu et al.

(10) Patent No.: US 12,709,773 B2
(45) Date of Patent: Aug. 18, 2026

(54) DYNAMIC MULTIPHASE REACTION IN ONE-POT FOR CRISPR/Cas-DERIVED ULTRA-SENSITIVE MOLECULAR DETECTION

(71) Applicant: University of Conecticut, Farmington, CT (US)

(72) Inventors: Changchun Liu, Farmington, CT (US); Kun Yin, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 959 days.

(21) Appl. No.: 17/790,277

(22) PCT Filed: Feb. 5, 2021

(86) PCT No.: PCT/US2021/016755
§ 371 (c)(1),
(2) Date: Jun. 30, 2022

(87) PCT Pub. No.: WO2021/158877
PCT Pub. Date: Aug. 12, 2021

(65) Prior Publication Data

US 2023/0091060 A1 Mar. 23, 2023

Related U.S. Application Data

(60) Provisional application No. 62/971,491, filed on Feb. 7, 2020.

(51) Int. Cl.

| | |
|---|---|
| *C12Q 1/6844* | (2018.01) |
| *C12N 9/12* | (2006.01) |
| *C12Q 1/6806* | (2018.01) |

(52) U.S. Cl.
CPC ......... *C12Q 1/6844* (2013.01); *C12N 9/1241* (2013.01); *C12Q 1/6806* (2013.01); *C12N 2310/20* (2017.05)

(58) Field of Classification Search
CPC ................ C12Q 1/6844; C12Q 1/6806; C12Q 2521/301; C12Q 2537/101; C12Q 2565/1015; C12N 9/1241; C12N 2310/20
See application file for complete search history.

(56) References Cited

U.S. PATENT DOCUMENTS

2018/0340219 A1 11/2018 Abudayyeh et al.
2019/0241954 A1 8/2019 Doudna et al.

OTHER PUBLICATIONS

Wang et al., Cas12aVDet: A CRISPR/Cas12a-Based Platform for Rapid and Visual Nucleic Acid Detection, Analytical Chemistry, Aug. 2019, 91, 12156-12161 (Year: 2019).*

(Continued)

*Primary Examiner* — Robert T. Crow
*Assistant Examiner* — Allison E Schloop
(74) *Attorney, Agent, or Firm* — CANTOR COLBURN LLP

(57) ABSTRACT

Described herein is an aqueous, miscible, multiphase, one-pot detection system including a first phase comprising a low density solution comprising a nucleic acid detection system; and a second phase in diffusive communication with the first phase, the second phase having a higher density than the first phase, and the second phase including a nucleic acid amplification system. Also included are multiwell plates and/or devices including the system and methods of detecting target nucleic acids.

20 Claims, 24 Drawing Sheets

(56) References Cited

OTHER PUBLICATIONS

Cheung et al., A one-pot, isothermal DNA sample preparation and amplification platform utilizing aqueous two-phase system, Analytical and Bioanalytical Chemistry, Jun. 2018, 410, 5255-5263 (Year: 2018).*
TwistDx, TwistAmp DNA Amplification Kits, 2016, 1-80 (Year: 2016).*
Moon et al., Recent advances in the CRISPR genome editing tool set, Experimental and Molecular Medicine, Nov. 2019, 51, 1-11 (Year: 2019).*
Freire et al., Aqueous biphasic systems composed of a water-stable ionic liquid + carbohydrates and their applications, Green Chemistry, 2011, 13, 1536-1545 (Year: 2011).*
Morandeira et al., Setting the Foundations of Aqueous Three-Phase Systems (A3PS) in the Quest for a Rational Design, ChemPhysChem, Oct. 2019, 20, 3311-3321 (Year: 2019).*
Harrington, Programmed DNA destruction by miniature CRISPR-Cas14 enzymes, Science, Oct. 2018, 362, 1-4 (Year: 2018).*
Bai, J. et al.; "Cas12a-based on-site and rapid nucleic acid detection of African swine fever"; Frontiers in Microbiology, vol. 10, Article No. 2830; 2019; pp. 1-9.
International Search Report and Written Opinion for International Application PCT/US2021/016755; International Filing Date: Feb. 5, 2021; Date of Mailing: Jun. 9, 2021; 9 pages.
Yin, K., et al.; "Dynamic aqueous multiphase reaction system for one-pot CRISPR-Cas12a-based ultrasensitive and quantitative molecular diagnosis"; Analytical Chemistry, vol. 92; 2020; pp. 8561-8568.
He et al. (The CRISPR/Cas System: A Customizable Toolbox for Molecular Detection. Genes. 2023. 14(4):850.
Li et al. "HOLMESv2: a CRISPR-Cas 12b-assisted platform for nucleic acid detection and DNA methylation quantitation", ACS Synthetic Biology, Sep. 18, 2019, vol. 8, pp. 2228-2237.
Tang et al. (The CRISPR-Cas toolbox for analytical and diagnostic assay development. Chem. Soc. Rev.2001. 50, 11844.
Weng et al. (CRISPR-Cas Biochemistry and CRISPR-Based Molecular Diagnostics. Angrew. Chem. Int. Ed. 2023. 62, e02214987.

* cited by examiner

THRESHOLD TIME (min)
60
50
40
30
20
10
y=70.07-15.79x
r2=0.992
1
2
3
Log (HPV16 COPIES/REACTION
NC
1
2
3
1.00x10^4
7.50x10^3
5.00x10^3
2.50x10^3
0.00
RFU
NEGATIVE CONTROL
HPV16
HPV18
HPV31
0
15
30
45
60
TIME (min)

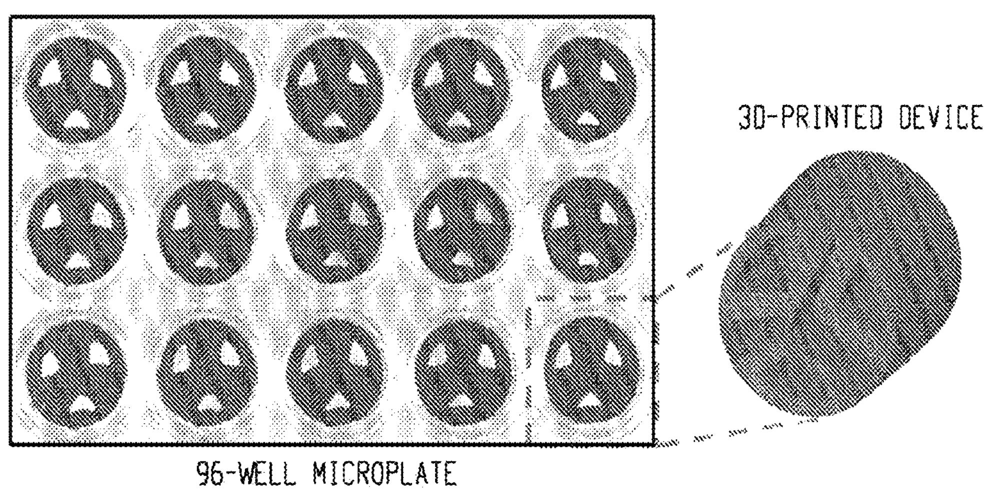
Fig. 9C
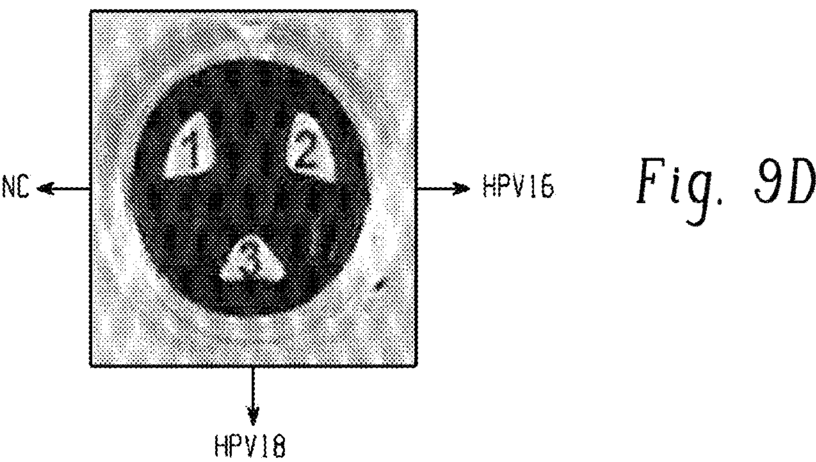
Fig. 9D
Fig. 9E
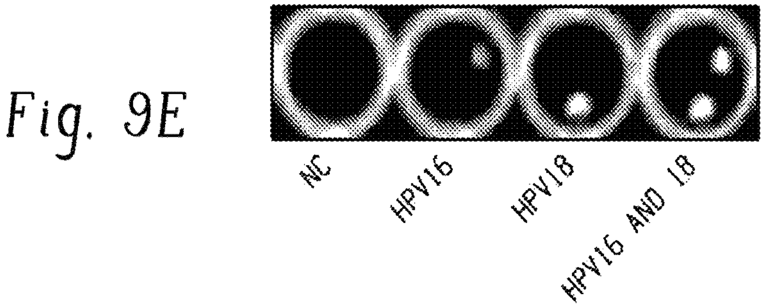

DYNAMIC MULTIPHASE REACTION IN ONE-POT FOR CRISPR/Cas-DERIVED ULTRA-SENSITIVE MOLECULAR DETECTION

CROSS-REFERENCE TO RELATED APPLICATIONS

This application is a National Stage application of PCT/US2021/016755, filed Feb. 5, 2021, which claims priority to U.S. Provisional Application 62/971,491 filed on Feb. 7, 2020, which are incorporated herein by reference in their entirety.

STATEMENT REGARDING FEDERALLY SPONSORED RESEARCH & DEVELOPMENT

This invention was made with government support under R01CA214072 awarded by the National Institutes of Health. The government has certain rights in the invention.

FIELD OF THE DISCLOSURE

The present disclosure is related to systems, devices and methods for the one-pot detection of molecules, including combined amplification and nucleic acid detection such as CRISPR/Cas detection.

BACKGROUND

Molecular diagnostics is critical for the identification of pathogens and genotyping, which makes an outstanding contribution to clinical diagnostics, biosecurity and environmental monitoring. Nucleic acid testing is a major molecular diagnostic technique, including nucleic acid hybridization, qPCR and isothermal amplification methods. These existing techniques require tedious sample treatment and sophisticated systems, which rely on well-trained operators and dedicated instruments. Therefore, there is an urgent need to develop novel nucleic acid testing methods to achieve simple, rapid, ultra-sensitive and high-selective detection.

BRIEF SUMMARY

In one aspect, an aqueous, miscible, multiphase, one-pot detection system comprises a first phase comprising a low density solution comprising a nucleic acid detection system; and a second phase in diffusive communication with the first phase, the second phase having a higher density than the first phase, and the second phase comprising a nucleic acid amplification system.

Also described are multiwell plates and/or devices comprising the above-described systems.

In an aspect, a method of detecting a target nucleic acid in a nucleic acid sample suspected of containing the target nucleic acid comprises providing a second phase comprising a high density solution, a nucleic acid amplification system, forward and reverse primers for amplification of the target nucleic acid, and the nucleic acid sample suspected of containing the target nucleic acid; providing a first phase in diffusive communication with the second phase, the first phase having a lower density than the second phase, and the first phase comprising a nucleic acid detection system comprising a detectable label; and amplifying the target nucleic acid in the second phase for a time sufficient to provide amplified target nucleic acid and to allow the amplified target nucleic acid to diffuse to the first layer, wherein diffusion of the amplified target nucleic acid to the first layer activates the nucleic acid detection system and turns on the detectable label providing detection of the target nucleic acid in the sample.

BRIEF DESCRIPTION OF THE DRAWINGS

FIG. 9A-E illustrates clinical sample detection. 9A illustrates clinical sample detection using qPCR and RPA-CRISPR/Cas12a quantitative detection in aqueous two-phase system, respectively. 9B shows multiplex detection of HPV16 and HPV18 in PCR tubes. The right figure was the real-time fluorescent signal collected by PCR machine. 9C shows a 3D-printed device in a microplate. 9D shows the three chambers of a 3D-printed device (1: without crRNA, 2: with HPV16 crRNA and 3: with HPV18 crRNA). 9E shows a fluorescent image of high-throughput multiplex detection taken by a ChemiDoc™ MP Imaging System.

Figure 1:
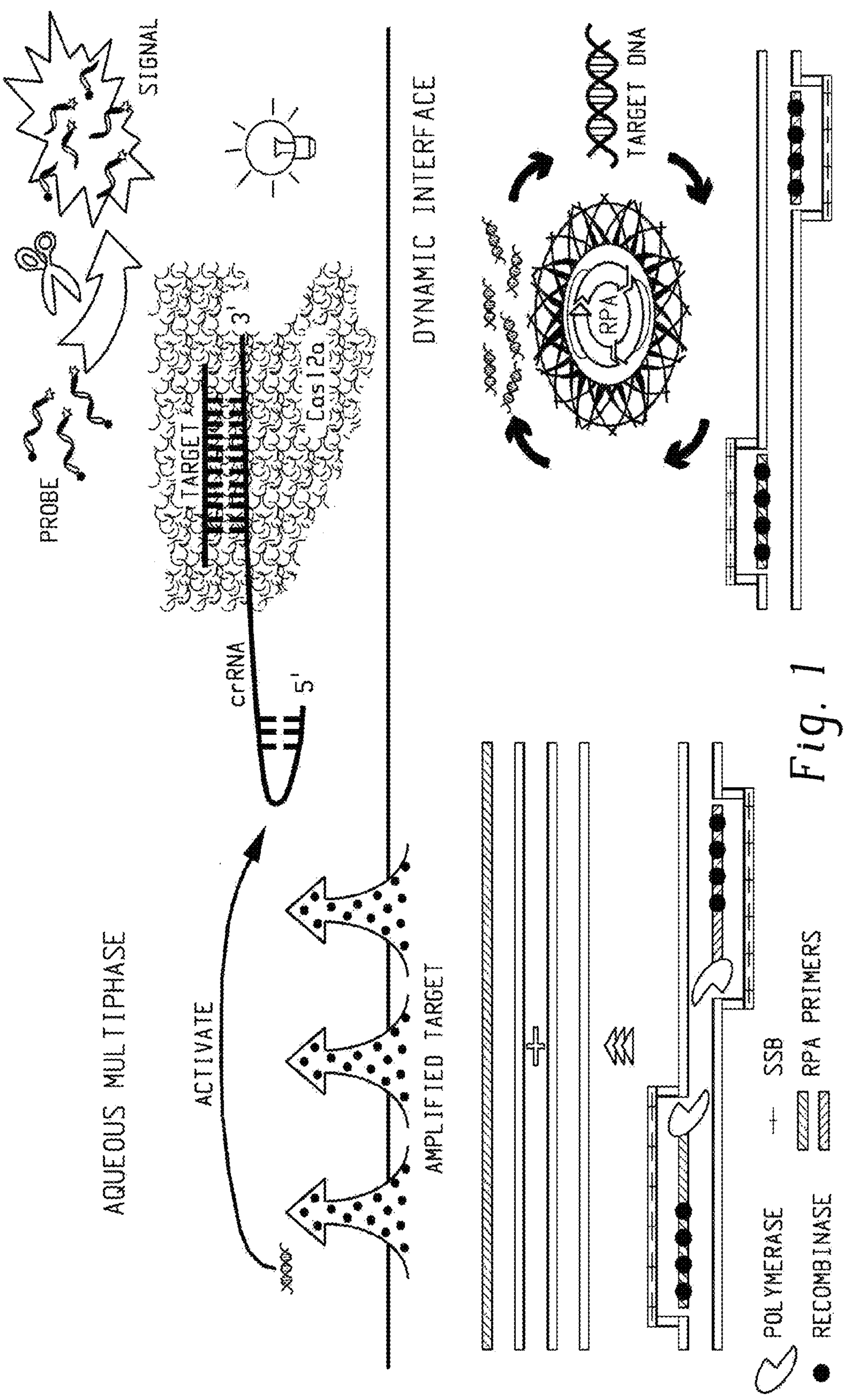
FIG. 1 shows the over-all design of a dynamic multiphase reaction. The amplified target during the RPA reaction in the bottom phase can dynamically diffuse to the upper phase and trigger the trans cleavage activity of CRISPR/Cas12a to complete detection.

The above-described and other features will be appreciated and understood by those skilled in the art from the following detailed description, drawings, and appended claims.

DETAILED DESCRIPTION

The CRISPR/Cas system, as a revolutionary gene-editing technique, has been widely applied in epigenetic engineering, gene regulation and genetic screening. Besides gene editing function as a 'magic wand', it also shows great promise for the next-generation of rapid and highly sensitive nucleic acid detection. In a CRISPR/Cas system, pre-CRISPR RNA (crRNA) serves as the guide to navigate Cas effectors and further possesses target-dependent cleavage activity. A series of Cas effectors including Cas9, Cas12a and Cas13 have been developed to establish CRISPR/Cas-based nucleic acid biosensing systems. Combined with nucleic acid amplification, the Cas9 effector has been harnessed to create nucleic acid sequence-based amplification (NASBA)-CRISPR cleavage to realize pathogen genotyping and single nucleotide polymorphisms (SNPs) discrimination. Unlike the Cas9 effector, the Cas12a and Cas13 endonucleases have collateral cleavage activities on single stranded DNA (ssDNA). The trans cleavage activity of the Cas12a and Cas13 endonucleases can be activated once they recognize their RNA or DNA targets, and they indiscriminately cleave a collateral ssDNA reporter with specific high sensitivity. Integrating Cas and Cas13 endonucleases with target amplification such as recombinase polymerase amplification (RPA), attomolar sensitivity can be achieved through a CRISPR biosensing system, which promises significant advances in molecular diagnostics. However, the target amplification and detection processes are required to be separated, which increases the risk of aerosol contamination during uncapping operation as well as the complexity, which limits its point-of-care application.

Described herein is a dynamic multiphase reaction system in one-pot to address this challenge, where RPA and CRISPR/Cas, for example, are separated in different phases with their optimal buffer to realize the highest efficiency. The amplified target by RPA can further trigger the trans cleavage activity of CRISPR/Cas to complete detection through dynamic diffusion. Compared with RPA and CRISPR/Cas directly mixed in one-pot, the multiphase reaction exhibits 100-times higher intensity with molecular level sensitivity and shortening of reaction time. As shown in the examples, clinical human swab samples are tested for the detection of high-risk genotypes HPV16 and 18. The results indicate that the methodology has great potential in clinical pathogen detection with satisfied sensitivity and specificity. Combined with a 3D-printed device in a microplate, multiplex high-throughput detection can be realized. Additionally, the dynamic multiphase reaction system can directly detect spiked target nucleic acids in human plasma and avoid inhibition from a complicated biomatrix without sample pre-treatment, which greatly simplifies the detection process.

In an aspect, an aqueous, miscible, multiphase, one-pot detection system comprises a first phase comprising a low density solution comprising a nucleic acid detection system, and a second phase in diffusive communication with the first phase, the second phase having a higher density than the first phase, and the second phase comprising a nucleic acid amplification system.

The low density solution of the first phase and/or the high density solution of the second phase is a sucrose solution, polysucrose solution, glycerol, sorbitol, Ficoll® (copolymerized sucrose and epichlorohydrin), a dextran, or a combination thereof.

As used herein, a nucleic acid amplification system provides for both copying of a nucleic acid via the action of a primer or set of primers and for re-copying of said copy by a reverse primer or set of primers. This enables the generation of copies of the original nucleic acid at an exponential rate. Exemplary nucleic acid amplification systems include a Nucleic Acid Sequence Based Amplification (NASBA), Transcription Mediated Amplification (TMA), Helicase Dependent Amplification (HDA), Recombinase polymerase amplification (RPA), Strand Displacement Amplification (SDA), Loop-mediated Isothermal Amplification (LAMP), Chimera Displacement Reaction (RDC), Isothermal Chimeric Amplification of Nucleic Acids (ICAN), SMart Amplification Process (SMAP), Linear Isothermal Multimerization Amplification (LIMA), Dual-Priming Isothermal Amplification (DAMP), isothermal multiple-self-matching-initiated amplification (IMSA), or Self Extending Amplification (SEA). An exemplary recombinase polymerase amplification system comprises a single-stranded DNA-binding protein (SSB), a recombinase, and strand-displacing polymerase.

Exemplary nucleic acid detection systems comprise a Type V CRISPR/Cas detection system, a colorimetric detection system, a bioluminescence detection system, or an electrochemical detection system.

As described in US2019/0241954, type V CRISPR/Cas proteins (e.g., Cas 12 proteins such as Cpf1 (Cas12a) and C2c1 (Cas12b)) can promiscuously cleave non-targeted single stranded DNA (ssDNA) once activated by detection of a target DNA. Once a type V CRISPR/Cas effector protein (e.g., a Cas12 protein such as Cas12a, Cas12b, Cas12c, Cas12d, Cas12e) is activated by a crRNA, which occurs when a sample includes a target DNA to which the guide RNA hybridizes (i.e., the sample includes the targeted DNA), the protein becomes a nuclease that promiscuously cleaves ssDNAs (i.e., non-target ssDNAs, i.e., ssDNAs to which the guide sequence of the guide RNA does not hybridize). Thus, when the targeted DNA (double or single stranded) is present in the sample (e.g., in some cases above a threshold amount), the result is cleavage of ssDNAs in the sample, which can be detected using any convenient detection method (e.g., using a labeled single stranded detector DNA).

In an aspect, the nucleic acid detection system is a Type V CRISPR/Cas detection system comprising a Cas12a, Cas13, Cas9 or Cas 14 endonuclease, a CRISPR RNA (crRNA) comprising a complementary sequence to a target sequence, and a single-stranded reporter DNA comprising a detectable label.

Exemplary detectable labels include radionuclides, fluorophores such as fluorescein, rhodamine, Texas Red, Cy2, Cy3, Cy5, and the AlexaFluor® (Invitrogen, Carlsbad, Calif.) range of fluorophores, antibodies, gadolinium, gold, nanomaterials, horseradish peroxidase, alkaline phosphatase, derivatives thereof, and mixtures thereof.

In an exemplary bioluminescence detection system, expression of the luciferase gene can be engineered into the nucleic acid amplification system and detected by the nucleic acid detection system.

In an exemplary electrochemical detection system, DNA intercalating redox probes, redox-active enzymes such as horseradish peroxidase and alkaline phosphate, as well as nanoparticles such as cadmium sulfide nanoparticles (CdSNPs) can be used in electrochemical detection strategies.

In an aspect, the volume ratio of the top phase to the bottom phase is 1:10 to 10:1.

In an aspect, the system further comprises a third phase, the third phase having a higher density than the second phase, wherein the third phase is in diffusive contact with the second phase. The third phase can comprise a nucleic acid preparation system.

Also included herein are multiwell plates and/or devices such as 3D printed devices comprising the systems described herein.

In an aspect, a method of detecting a target nucleic acid in a nucleic acid sample suspected of containing the target nucleic acid comprises providing a second phase comprising a high density solution, a nucleic acid amplification system, forward and reverse primers for amplification of the target nucleic acid, and the nucleic acid sample suspected of containing the target nucleic acid; providing a first phase in diffusive communication with the second phase, the first phase having a lower density than the second phase, and the first phase comprising a nucleic acid detection system comprising a detectable label; and amplifying the target nucleic acid in the second phase for a time sufficient to provide amplified target nucleic acid and to allow the amplified target nucleic acid to diffuse to the first layer, wherein diffusion of the amplified target nucleic acid to the first layer activates the nucleic acid detection system and turns on the detectable label providing detection of the target nucleic acid in the sample.

Additional aspects of the system are described above.

In an aspect, the method further comprises providing a third phase, the third phase having a higher density than the second phase, wherein the third phase is in diffusive contact with the second phase, and wherein the third phase comprises an unpurified sample comprising the nucleic acid sample, wherein the nucleic acid sample diffuses from the third phase to the second phase. In a specific aspect, the unpurified sample is a blood sample, a saliva sample, or a tissue sample. Advantageously, the systems and methods described herein can be used to analyze unpurified samples.

In an aspect, the target nucleic acid is a pathogen DNA or RNA, or a biomarker of disease.

In a further aspect, amplifying is done at a temperature of 30° C. to 65° C.

The invention is further illustrated by the following non-limiting examples.

EXAMPLES Methods

Aqueous multiphase systems: Density-induced multiple aqueous phases were realized using increasing concentrations of sucrose solution. Stock solutions of sucrose in Milli-Q® water were prepared at high concentrations (10%-200%, w/w). To investigate the stability of the aqueous two-phase system, we added equal volumes (15 μL) of sucrose solution (from 10% to 50%, w/w) and water into different microcentrifuge tubes and incubated at 37° C. Sucrose solution from 10% to 30% were utilized to form aqueous multi-phase system with different dyes to indicate phase boundaries. (data not shown)

Connected RPA and CRISPR/Cas12a detection in an aqueous two-phase system: RPA using TwistAmp® Basic reagent (TwistDx™) was carried out in the bottom phase of the aqueous two-phase system and CRISPR/Cas12a detection proceeded in the top phase. Briefly, 0.48 μM forward and reverse primer, 14 mM magnesium acetate, and target mixed in lx rehydration buffer with sucrose inside was the bottom phase. 100 nM Cas12a, 50 nM ssDNA-FQ reporter, and 62.5 nM crRNA from Integrated DNA Technologies mixed in 1× cleavage buffer (100 mM KCl, 20 mM Tris-Cl (pH 7.8 at 25° C.), 5 mM $MgCl_2$, 50 μg $mL^{-1}$ heparin, 1% (v/v) glycerol and 1 mM DTT) was the top phase. Reactions were incubated in PCR tubes with reaction carried out at 37° C. on CFX96 Touch™ Real-Time PCR Detection System (Bio-Rad). After reaction, fluorescence signal images were collected using ChemiDoc™ MP Imaging System (Bio-Rad) and the bright-green signal could be recognized directly by the naked eye under blue light. The fluorescence signal intensity from different tubes was collected by a developed mobile App "Hue Analyzer".

Reaction optimization: To establish a dynamic multiphase boundary with an appropriate diffusion rate, the down-phase RPA reaction under different sucrose concentrations from 5% to 50% and top-phase CRISPR/Cas12a reaction in 1X cleavage buffer were carried out in PCR tubes at 37° C. for 2 hours. The volume ratio of top-phase to down-phase from 5:1 to 1:5 were also investigated for the reaction optimization.

Sensitivity and specificity: Ten-fold serial diluted HPV 16 or 18 DNA from 0 to $10^5$ copies were added into 20 μL RPA reaction phase with 10% sucrose and specific forward and reverse primers. HPV 16 and 18 specific crRNA was added into 10 μL CRISPR/Cas12a reaction phase, respectively. Reactions were incubated in PCR tubes at 37° C. for 1 h to evaluate the sensitivity of developed dynamic multiphase reaction system. To investigate the specificity, $10^4$ copies HPV 16, 18 and 31 DNA was added into 20 μL RPA reaction phase with 10% sucrose and HPV16 forward and reverse primers, respectively. HPV 16 crRNA was added into 10 μL CRISPR/Cas12a reaction phase. Reactions were incubated in PCR tubes at 37° C. for 1 h.

Multiplex detection and 3D-printed device in microplate: 0.48 μM HPV 16 and 18 forward and reverse primers were mixed together in 20 μL RPA reaction phase (10% sucrose). The specific crRNA was added into 10 μL CRISPR/Cas12a reaction phase and incubated in PCR tubes at 37° C. for 1 h to achieve multiplex detection. To realize high-throughput multiplex detection, a three-chamber microfluidic device was fabricated by 3D-printing, which can be inserted into the cells of 96-well microplate. 0.48 μM HPV 16 and 18 forward and reverse primers were mixed together in 70 μL RPA reaction phase with 10% sucrose and added to the bottom of cells. 3D-printed device was inserted into the cells and their three chambers was added with 10 μL CRISPR/Cas12a reaction without crRNA, with HPV16 cr RNA, and with HPV18 crRNA, respectively. Sealed by a Microseal® B Adhesive sealer (Bio-Rad) to avoid contamination, the image of 96-well microplate was taken by ChemiDoc™ MP Imaging System (Bio-Rad) after incubated at 37° C. for 1 h.

Human clinical swab sample collection and DNA purification: Clinical cervical swab samples were obtained from the Hospital of the University of Pennsylvania (IRB protocol #:829760). 500 μL samples were centrifuged at 1000×g for 2 min to collect cell pellets. The cell pellet was suspended in 200 μL PBS with 20 μL proteinase K. Purified DNA from cell pellet was obtained using DNeasy® Blood & Tissue Kit (Qiagen).

HPV spiked human plasma sample detection: Plasma samples were ordered from AcroMetrix™. $10^4$ copies HPV DNA was spiked into plasma samples and directly used for detection. An aqueous three-phase system was applied for RPA-CRISPR/Cas12a detection. A 10 μL plasma sample with 40% sucrose was the bottom phase. A 20 μL RPA reaction with 10% sucrose was the middle phase. A 10 μL CRISPR/Cas12a reaction solution was the top phase. For a negative control, a 10 μL plasma sample was mixed with 20 μL RPA reaction (10% sucrose) as the bottom phase and CRISPR/Cas12a reaction solution was the top phase. Reactions were incubated in PCR tubes at 37° C. for 1 h. To optimize the sucrose concentration in the bottom plasma phase, 20%, 40%, 60% and 80% sucrose solution was used in plasma samples as the bottom phase.

HPV spiked human plasma samples were detected by LAMP and PCR using anaqueous two-phase system. A 10 μL plasma sample with 40% sucrose was the bottom phase. A 20 μL LAMP or PCR solution was the top phase. For LAMP reaction, reactions were incubated in PCR tubes at 63° C. for 1 h. For PCR reaction, reactions included an initial hold step of at 95° C. for 10 min, followed by a two-step cycle of 15 s at 95° C. and 1 min at 57° C. for 60 cycles.

Example 1: Design of a Dynamic Multiphase Reaction

An aqueous multiphase system can be established spontaneously according to liquid density difference with a visually discernible interface. Compared with an overlay miscible solution of sucrose, the immiscible mixture can provide thermodynamically stable and molecularly sharp boundaries based on density, which owns great advantage and has been widely utilized for hydrodynamic fractionation and separation. However, the dynamic diffusing interface of a miscible multiphase system may offer an opportunity to combine incompatible, but correlative reactions together to achieve high reaction efficiency with simpler steps. A sucrose/water multiphase system is applied to achieve RPA-CRISPR/Cas12a molecular detection in one-pot. As shown in FIG. 1, target nucleic acids were firstly amplified by RPA reaction in the bottom-phase. Amplified nucleic acids could diffuse to the top-phase and activate the nonspecific trans cleavage activity of Cas12a with crRNA. The activated Cas12a further cleaved a fluorophore quencher (FQ)-labeled ssDNA probe to turn on a fluorescent signal and realize detection qualitatively or quantitatively. The dynamical interface diffusion is slow under 37° C. in aqueous two-phase system, which offers an independent but interrelated reaction condition (data not shown). Additionally, an aqueous multiphase reaction system to connect multiple reactions is also available through overlaying sucrose solution step-gradient in density (data not shown).

Figures 2A, 2B, 2C:
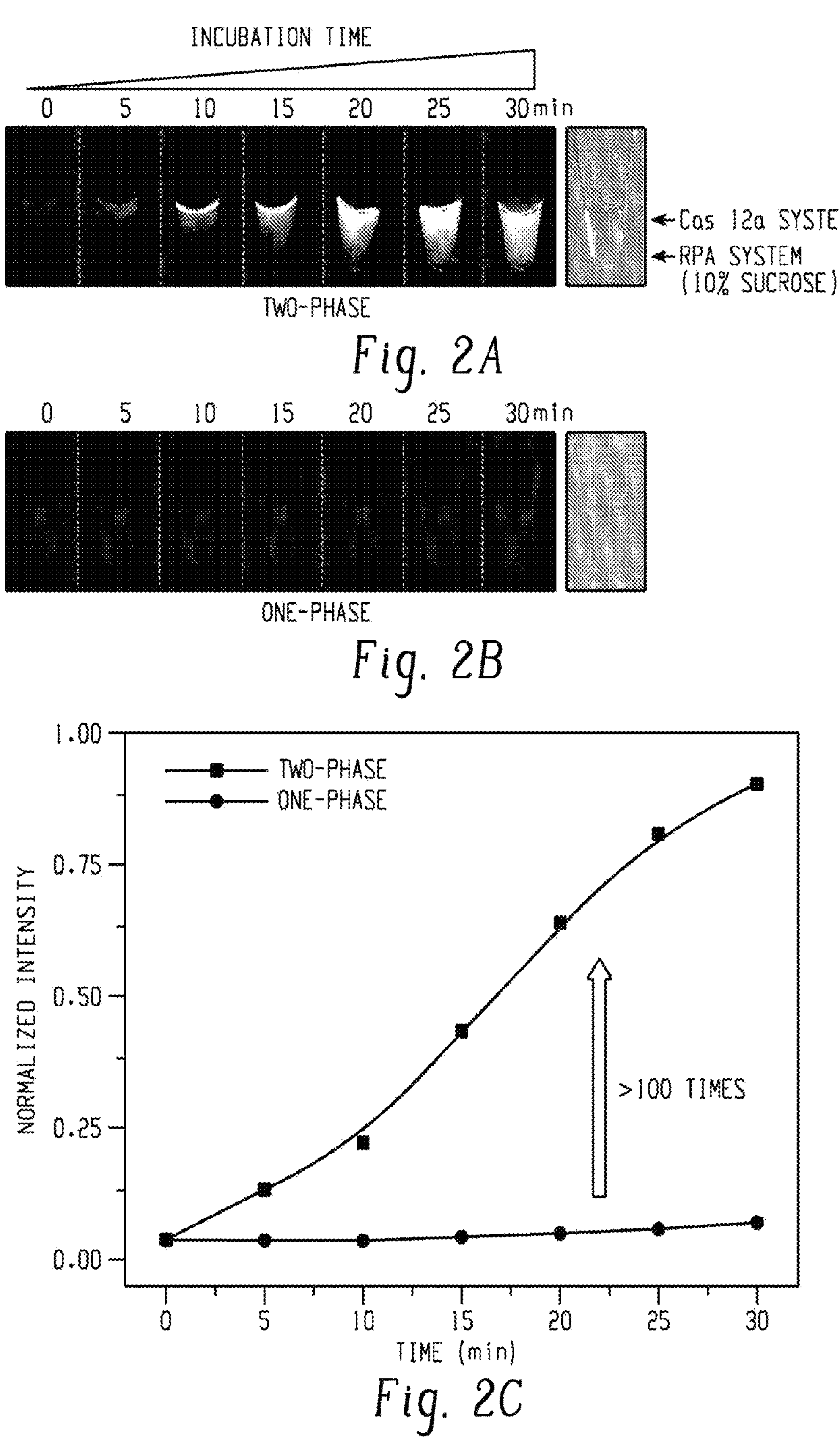
FIG. 2A-C illustrates RPA-CRISPR/Cas12a detection. 2A shows the connected RPA-CRISPR/Cas12a reaction in an aqueous two-phase system. 2B shows the RPA-CRISPR/Cas12a reaction in a one-phase system. 2C shows the fluorescent intensity of RPA-CRISPR/Cas12a reaction under different times in aqueous two-phase and one-phase system, respectively.

Example 2: Evaluation of RPA-CRISPR/Cas12a Detection in Aqueous Two-Phase System CRISPR/Cas12a reaction buffer has been confirmed to inhibit an RPA reaction. The activated Cas12a can also cleavage target nucleic acids (original or amplified nucleic acids during RPA reaction) because of its nonspecific trans cleavage activity to further slow the detection process. Therefore, the sensitive and selective RPA-CRISPR/Cas12a detection requires separated target amplification and detection processes, which may increase the risk of cross-contamination during the uncapping operation. Additionally, the volume ratio of CRISPR/Cas12a to RPA is optimized to 1:10, which will limit the inhibiting effect of CRISPR/Cas12a reaction buffer on RPA reaction to achieve better detection performance But, at the same time, the fluorescent signal would decrease because of the low percentage of CRISPR/Cas12a in the detection system. To address this challenge, an aqueous two-phase system is applied to realize connected RPA-CRISPR/Cas12a detection in one-pot. $10^4$ copies of HPV16 was added into the 20 μL RPA bottom phase with 10% sucrose and 10 μL CRISPR/Cas12a as the top phase. As shown in FIG. 2A, an obvious fluorescent signal can be observed after a 30 min incubation. The fluorescent signal occurred firstly at the top phase where CRISPR/Cas12a located and diffused to the whole tube with ongoing reaction going, which confirmed the independent reaction and dynamic diffusion during the detection process. In comparison, no fluorescent signal can be observed in a one-phase system unless incubated at 37° C. for 48 hours (FIG. 2B, data not shown). As shown in FIG. 2C, the signal from an aqueous two-phase system is about 100 times higher than one-phase reaction under the same incubation time and over 100 times faster to generate similar recognizable fluorescent signal.

Figure 3A:
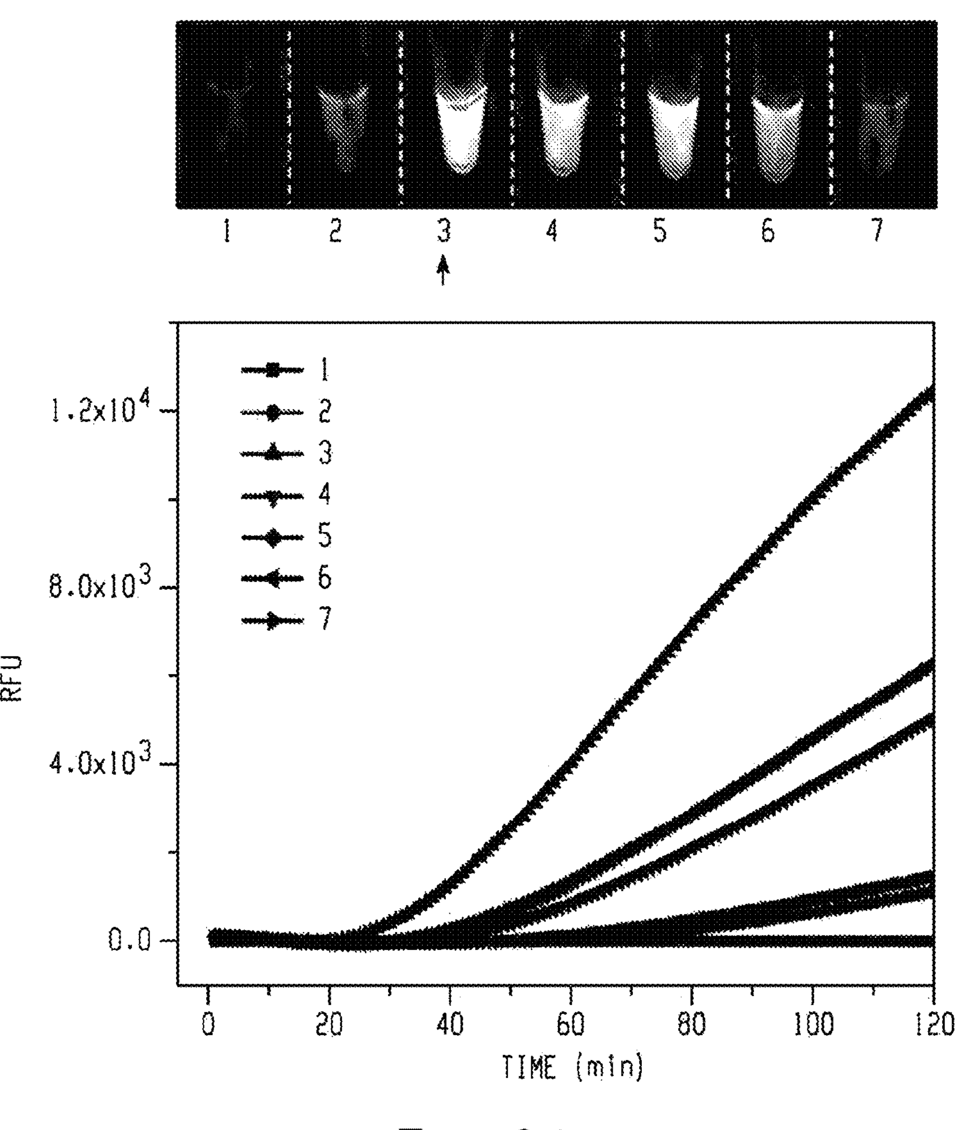
FIG. 3A-F shows reaction optimization. 3A illustrates how the series sucrose concentration (0%, 5%, 10%, 20%, 30%, 40%, and 50%) in RPA works as the bottom phase and CRISPR/Cas12a detection buffer works as the top phase. 3B shows the threshold time of different groups in 3A. 3C shows the RFU of different groups in 3D after incubation at 37° C. for 120 mins. 3D shows reaction under series volume ratios (1:5, 1:2, 1:1, 2:1, 5:1) of an RPA bottom phase and a CRISPR/Cas12a top phase. 3E shows the threshold time of different groups in 3D. 3F shows the RFU of different groups in 3D after incubation at 37° C. for 120 mins (n=3).
Figure 3B:
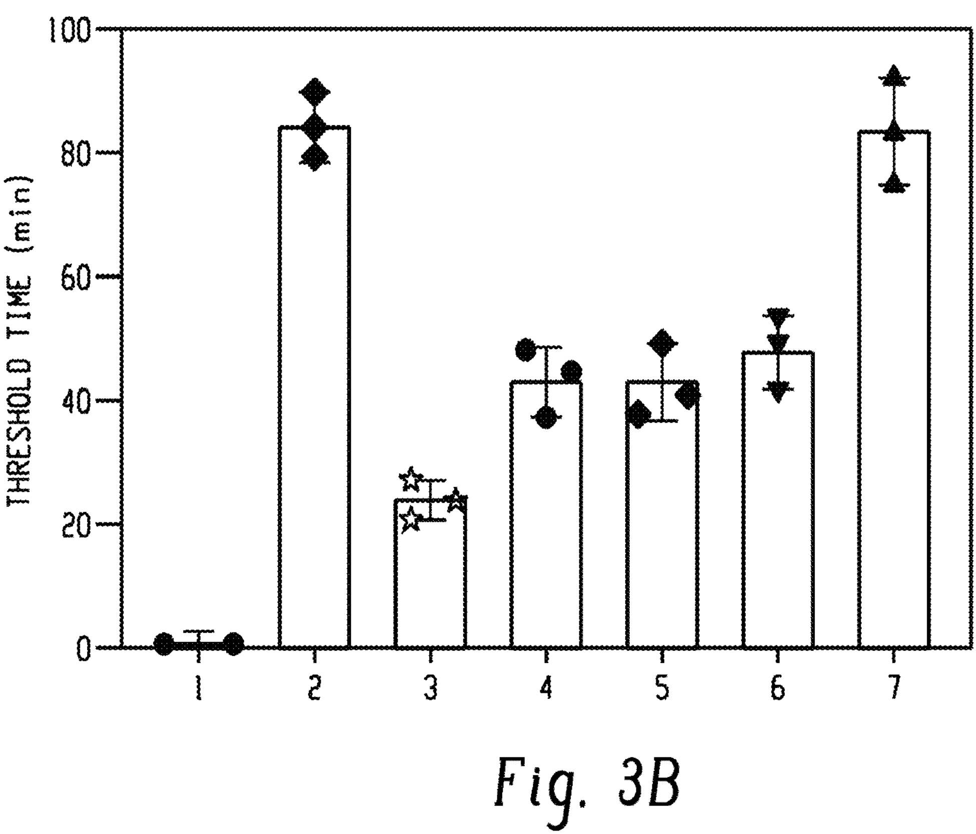
Figure 3C:
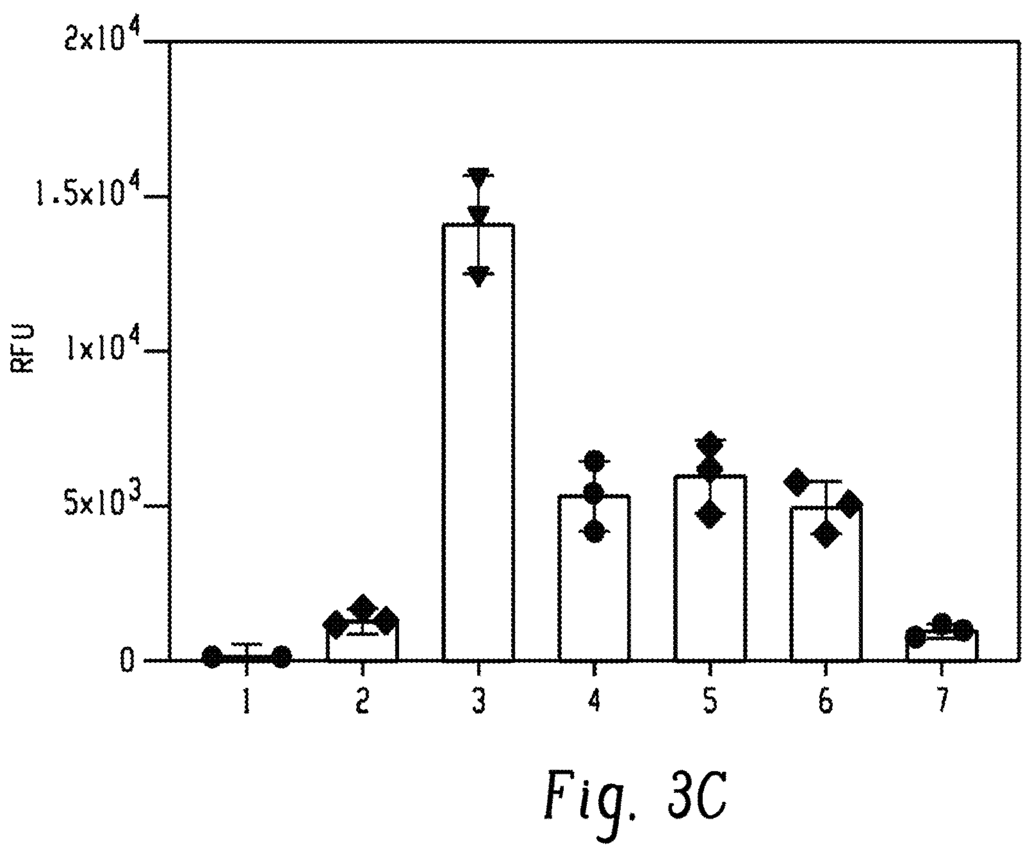
Figure 3D:
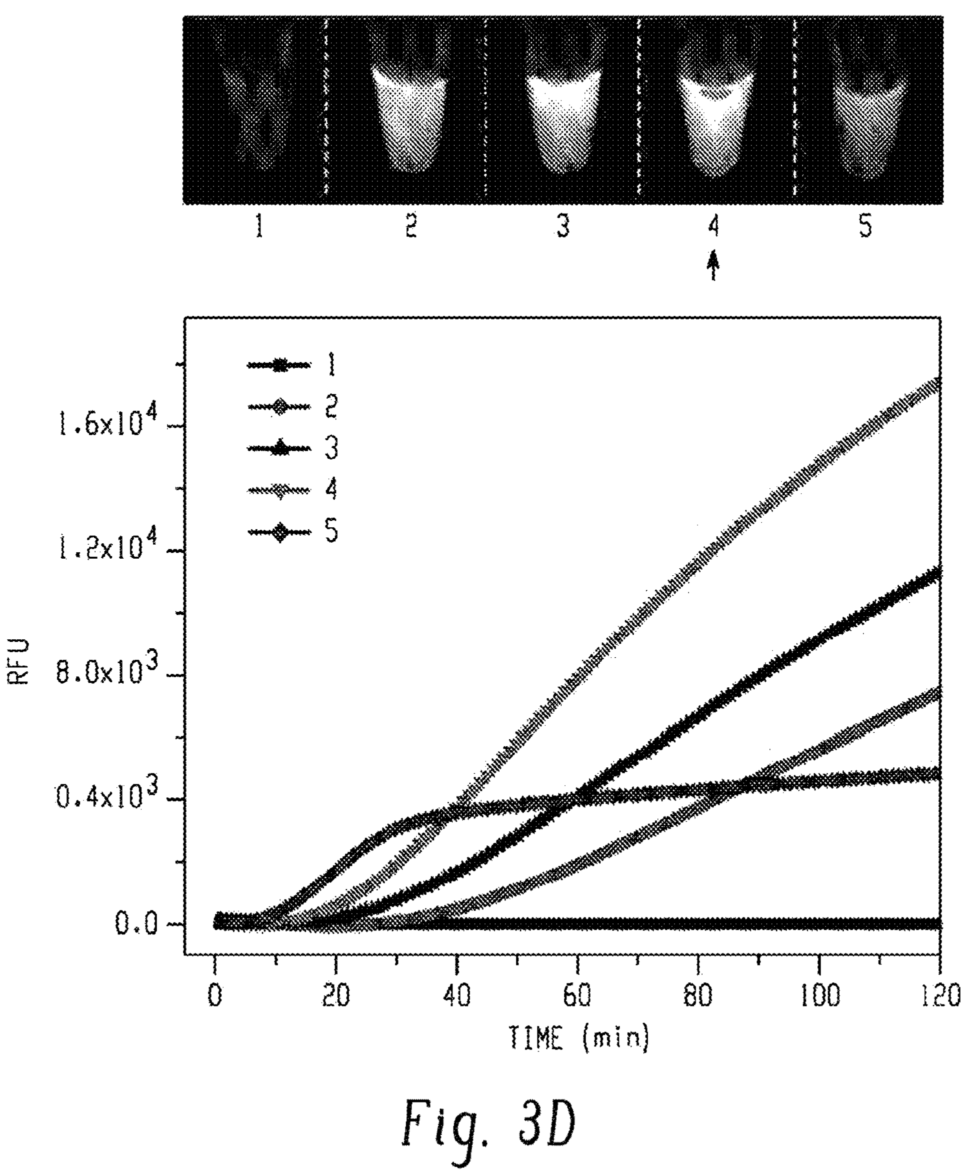
Figure 3E:
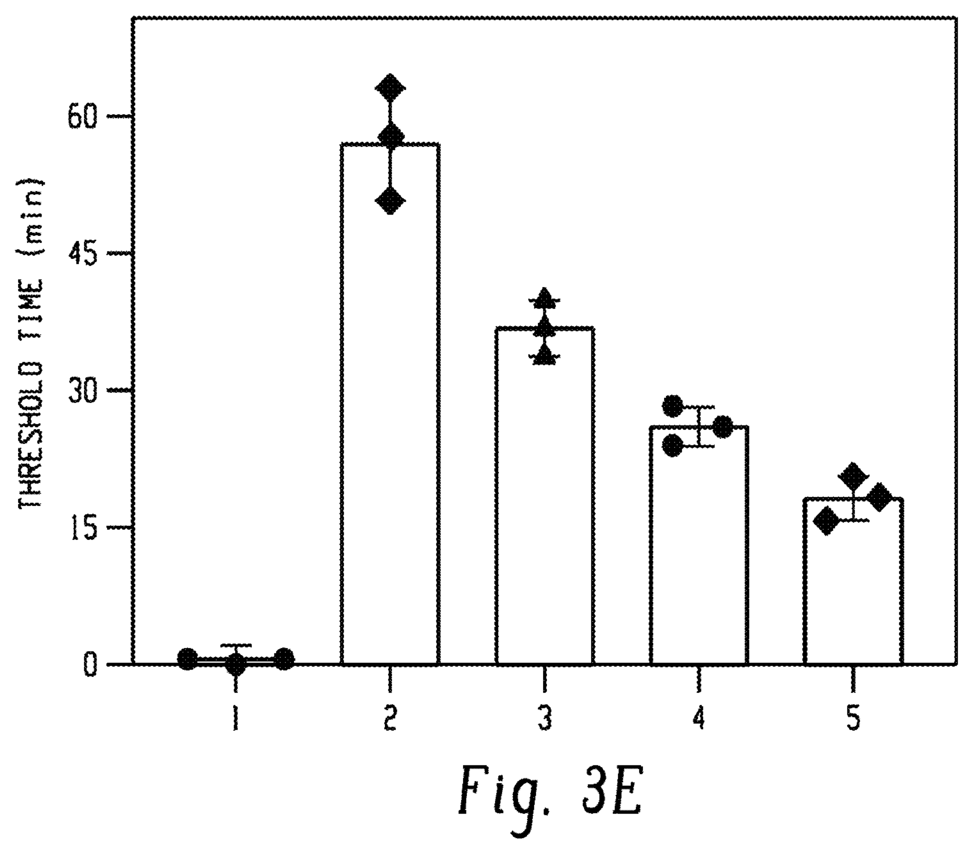
Figure 3F:
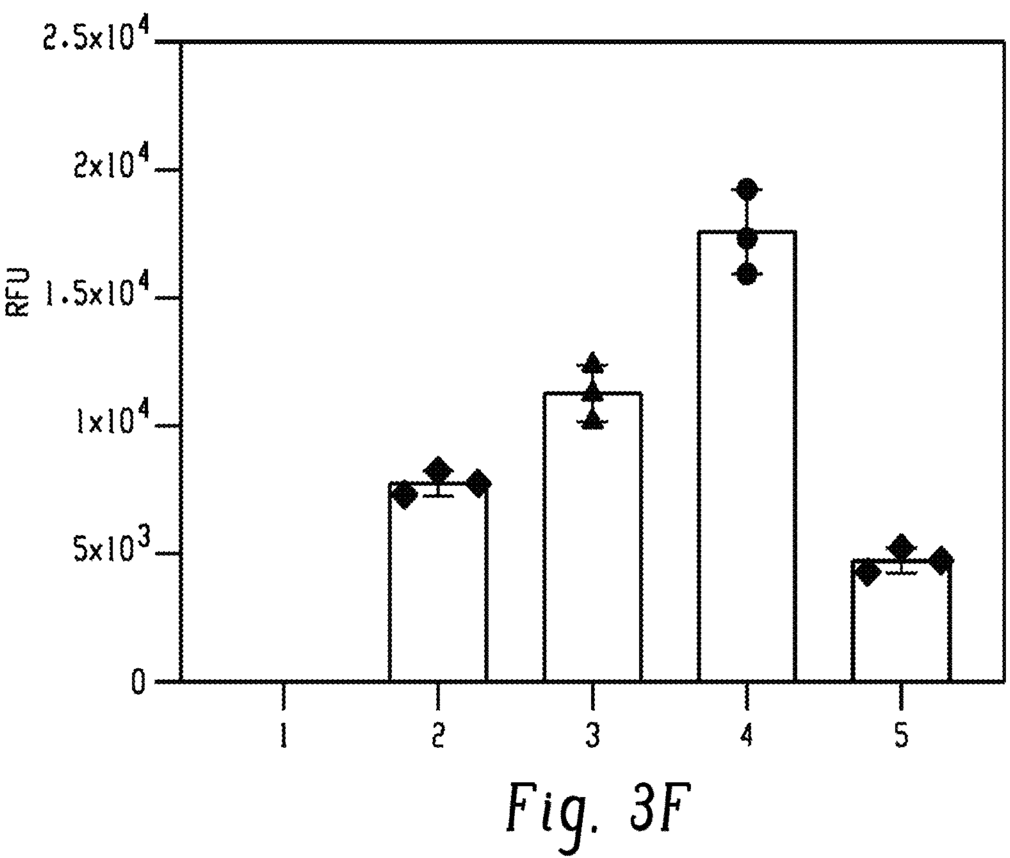

Example 3: Optimization of Aqueous Two-Phase System for RPA-CRISPR/Cas12a Detection RPA is a simple, fast, and isothermal amplification method whose optimal temperature ranges from 37 to 42° C. with high sensitivity. Three core enzymes including a single-stranded DNA-binding protein (SSB), a recombinase, and strand-displacing polymerase are the key contributions to the high amplification efficiency. Although RPA has a high tolerance to inhibitors, its efficiency will be inhibited by the CRISPR/Cas12a detection buffer. Therefore, the RPA is required to be carried out under independent reaction conditions. Then the amplicon needs to be added into CRISPR/Cas12a buffer to activate Cas12a and start the detection process, which is a challenge to achieve in one-pot detection. In this study, the bottom phase in an aqueous two-phase system can provide an independent reaction condition for RPA through density-driven phase separation and a sucrose hydrogen bond network. The amplicon can diffuse to the top phase to trigger the trans cleavage activity of CRISPR/Cas12a and complete detection. Therefore, the diffusion rate between the two-phases is the key point to connect these two incompatible but correlative reactions. The sucrose concentration and the volume ratio of the bottom and top phases are the main factors affecting the dynamic diffusion, which is optimized to realize the best performance. The viscosity of the solution is also decoupled with sucrose concentration to influence the diffusion. Therefore, to optimize sucrose concentration, $10^4$ copies human papillomavirus (HPV)16 DNA was added into 20 μL RPA reaction with series sucrose solution from 5% to 50% as the bottom-phase and 10 μL CRISPR/Cas12a detection buffer as the top-phase in PCR tubes, which was incubated at 37° C. for 2 hours. The real-time signal was collected by PCR machine and the fluorescent image was taken by ChemiDoc™ MP Imaging System (FIG. 3A). As shown in FIG. 3A-C, RPA reaction with 10% sucrose exhibited the highest fluorescent signal with the shortest threshold time. Next, the series volume ratio of RPA bottom phase (10% sucrose) and CRISPR/Cas12a top phase from 1:5 to 5:1 was investigated. As shown in FIG. 3D-F, the fastest reaction could be achieved in volume ratio 5:1 but its fluorescent intensity was much lower than the reaction in volume ratio 2:1, which was very important for visual detection and distinguish from background. Therefore, 20 μL RPA bottom phase (10% sucrose) and 10 μL CRISPR/Cas12a top phase was used for RPA-CRISPR/Cas12a detection in aqueous two-phase system.

Example 4: RPA-CRISPR/Cas12a Quantitative Detection in Aqueous Two-Phase System

Figure 4A:
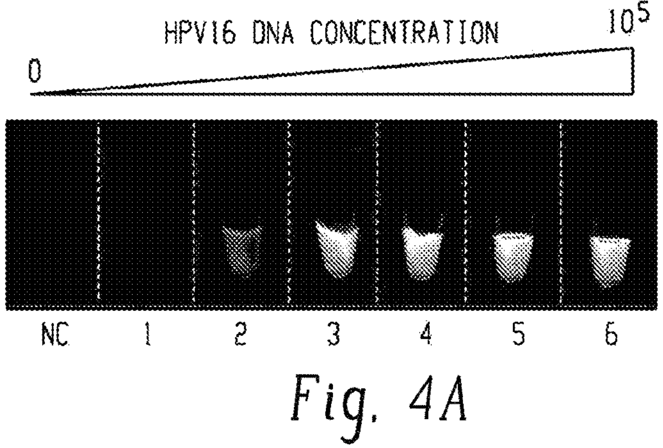
FIG. 4A-D illustrates HPV 16 DNA detection by a separated RPA-CRISPR/Cas12a method. Ten-fold serial diluted HPV 16 DNA (0, 1, 10, $10^2$, $10^3$, $10^4$, $10^5$ copies/reaction) was added into a 20 μL RPA reaction and incubated at 37° C. for 20 min. Then 2 μL RPA solution was added into 18 μL of CRISPR/Cas12a detection buffer and incubated at 37° C. for another 60 min. 4A shows a fluorescent image after reaction taken by a ChemiDoc™ MP Imaging System. 4B shows a fluorescent image taken by camera under blue light. 4C shows a real-time fluorescent signal collected by a PCR machine. 4D illustrates the linear relationship between the threshold time and HPV16 concentration. (n=3).
Figure 4B:
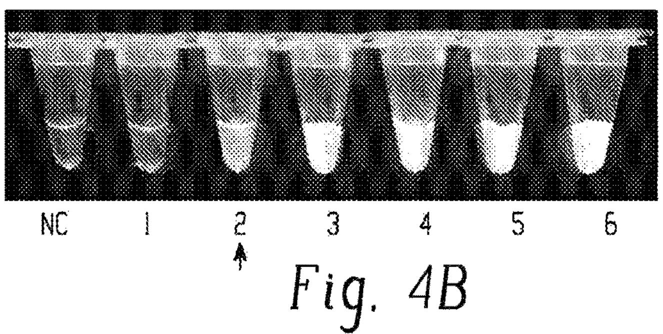
Figure 4C:
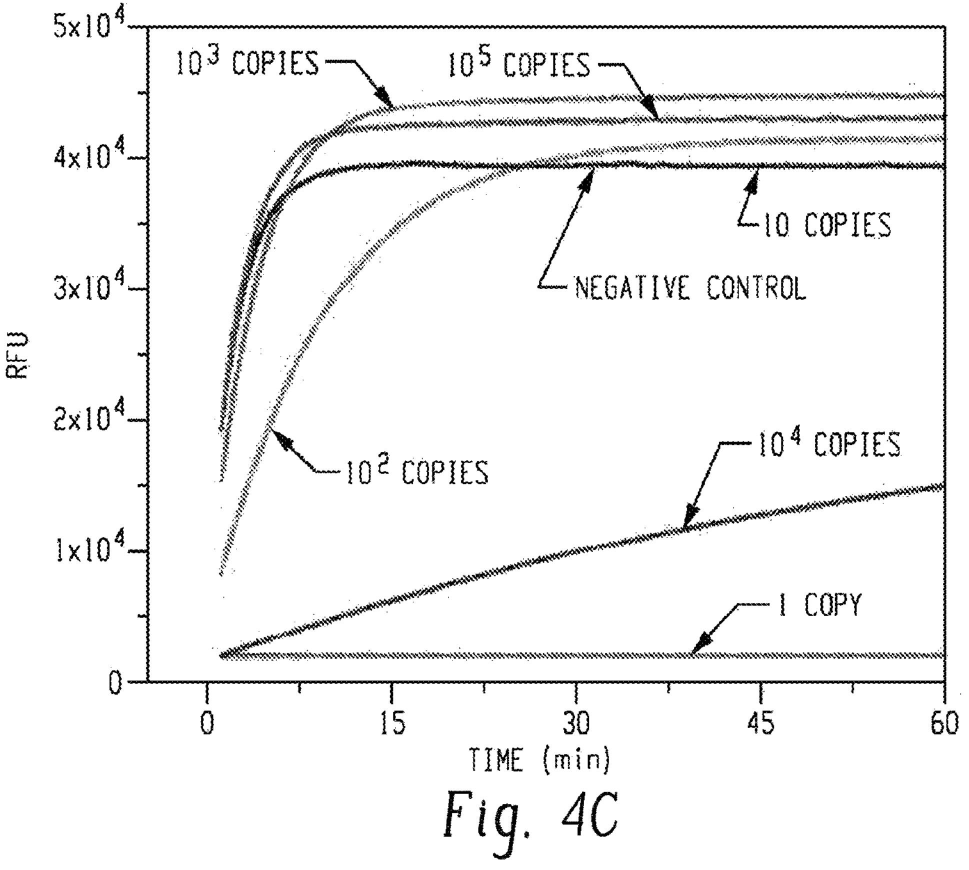
Figure 4D:
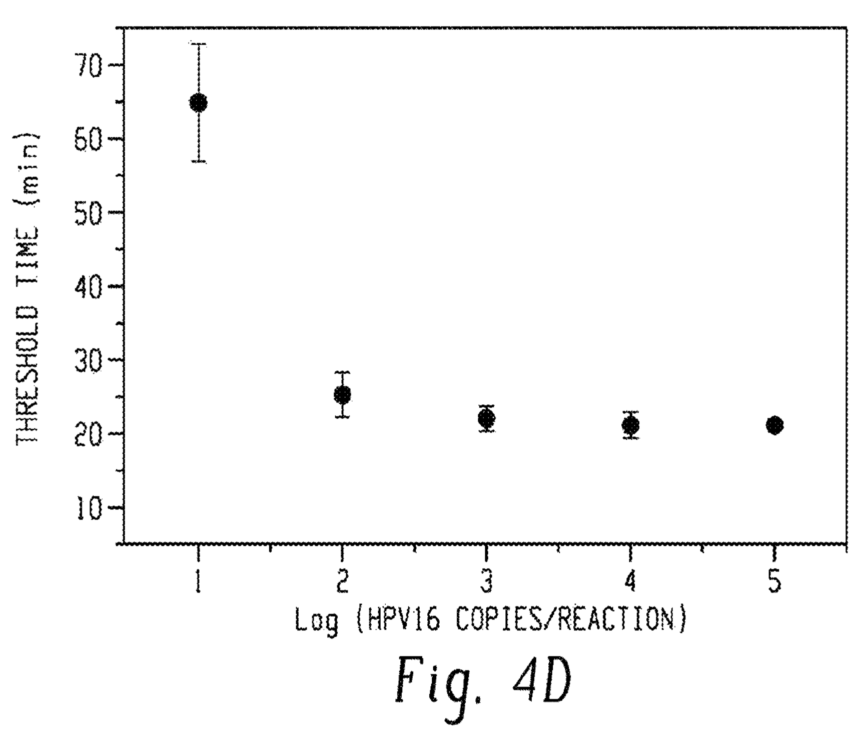
Figure 5A:
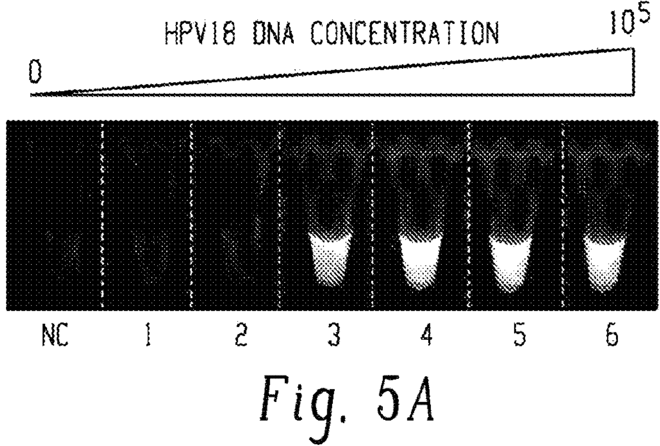
FIG. 5A-D illustrates HPV 18 DNA detection by a separated RPA-CRISPR/Cas12a method. Ten-fold serial diluted HPV 18 DNA (0, 1, 10, $10^2$, $10^3$, $10^4$, $10^5$ copies/reaction) was added into a 20 μL RPA reaction and incubated at 37° C. for 20 min. Then 2 μL RPA solution was added into 18 μL of CRISPR/Cas12a detection buffer and incubated at 37° C. for another 60 min. 5A shows a fluorescent image after reaction taken by a ChemiDoc™ MP Imaging System. 5B shows a fluorescent image taken by camera under blue light. 5C shows a real-time fluorescent signal collected by PCR machine. 5D illustrates the linear relationship between the threshold time and HPV18 concentration. (n=3)
Figure 5B:
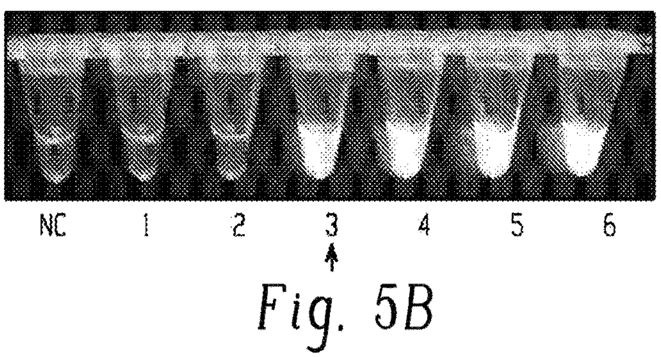
Figure 5C:
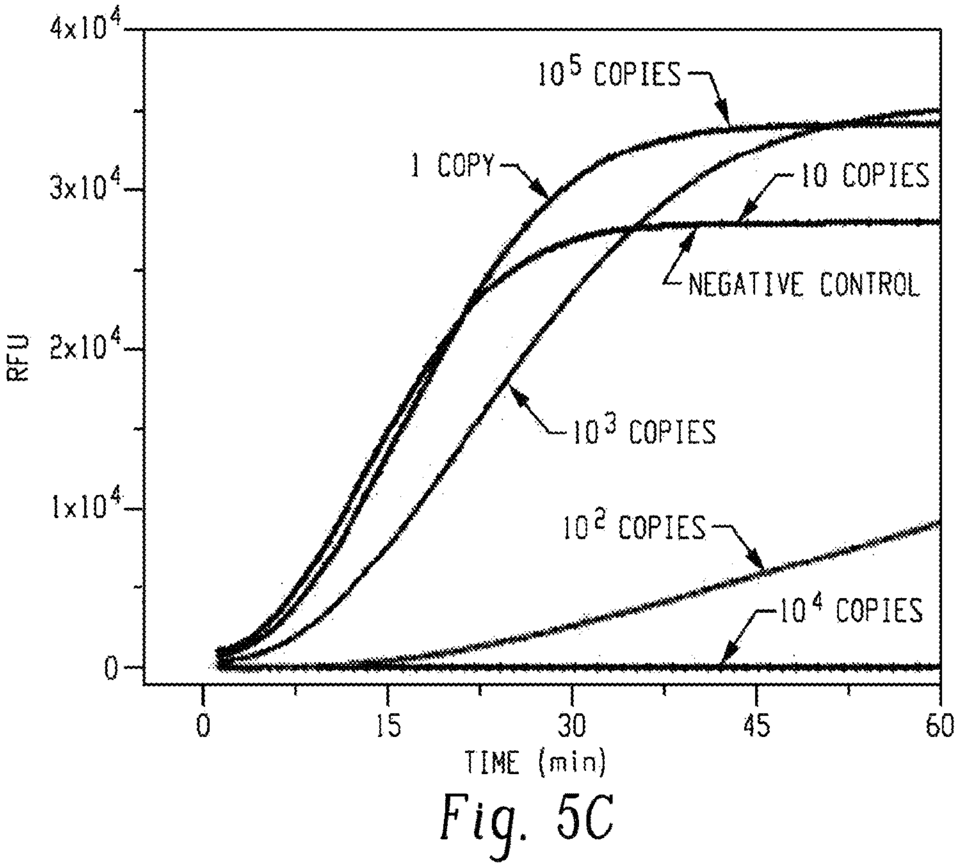
Figure 5D:
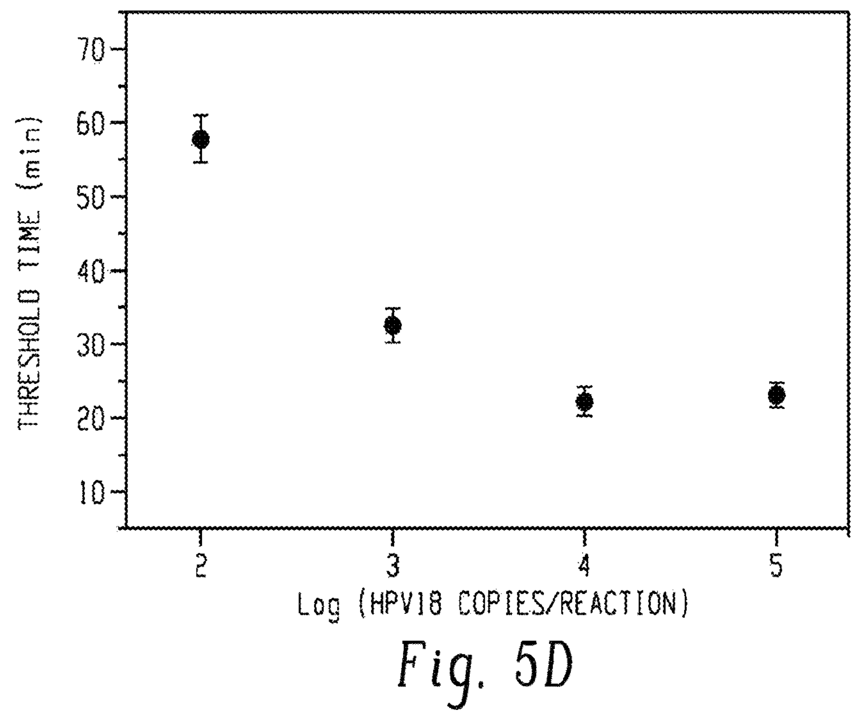
Figure 6A:
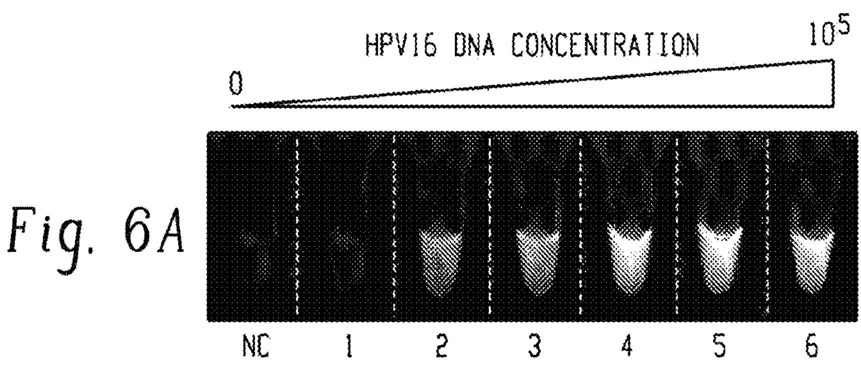
FIG. 6A-E illustrates quantitative detection. 6A-D show ten-fold serial diluted HPV 16 DNA (0, 1, 10, $10^2$, $10^3$, $10^4$, $10^5$ copies/reaction) was added into a 20 μL RPA reaction bottom phase (with 10% sucrose and specific primers) in the aqueous two-phase system and incubated at 37° C. for 1 hour. 6A shows a fluorescent image after reaction taken by a ChemiDoc™ MP Imaging System. 6B shows a fluorescent image taken by camera under blue light. 6C shows a real-time fluorescent signal collected by PCR machine. 6D illustrates the linear relationship between the threshold time and HPV16 concentration. (n=3). 6E illustrates the selective detection of $10^4$ copies HPV 16 DNA over HPV18 and HPV31 using RPA-CRISPR/Cas12a detection in an aqueous two-phase system.
Figure 6B:
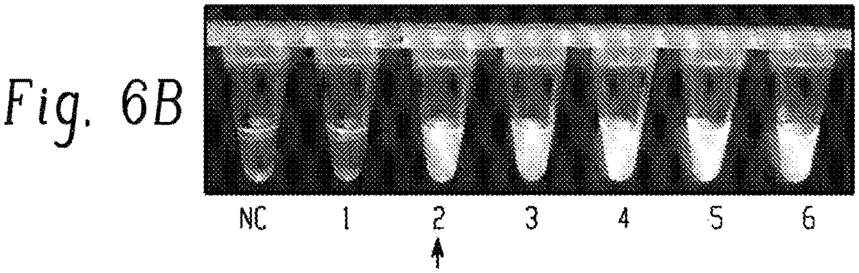
Figure 6C:
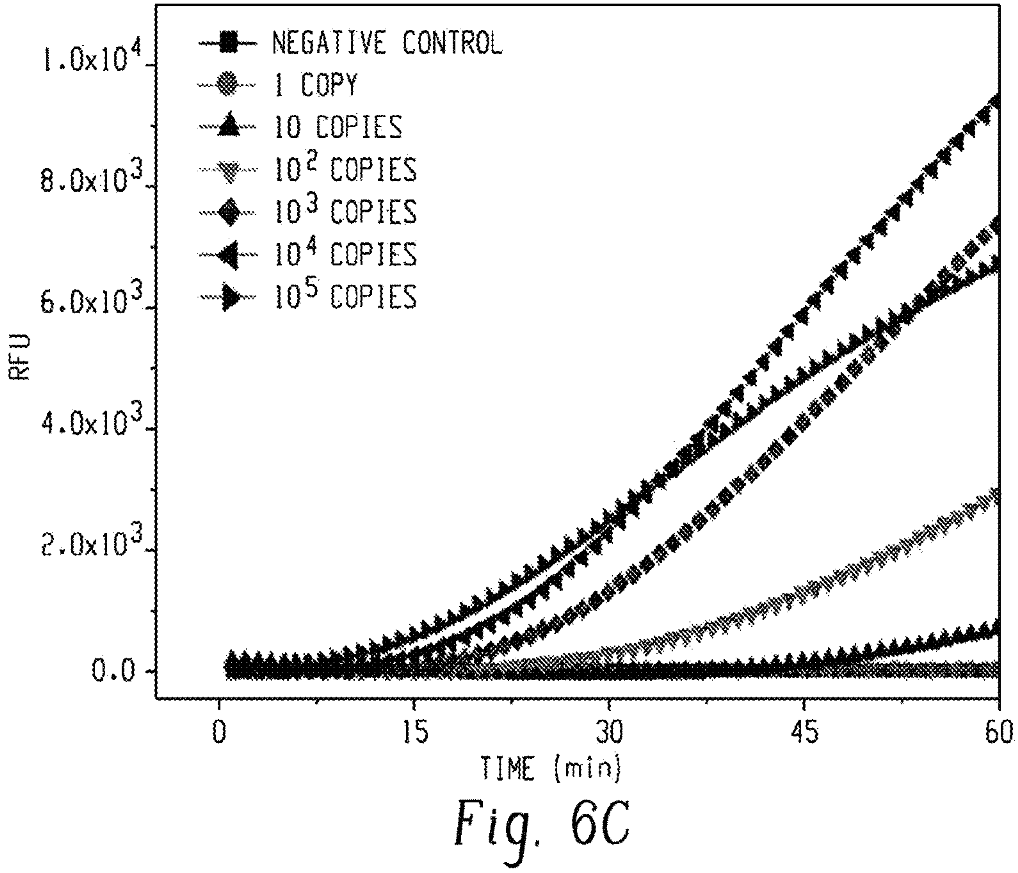
Figures 6D, 6E:
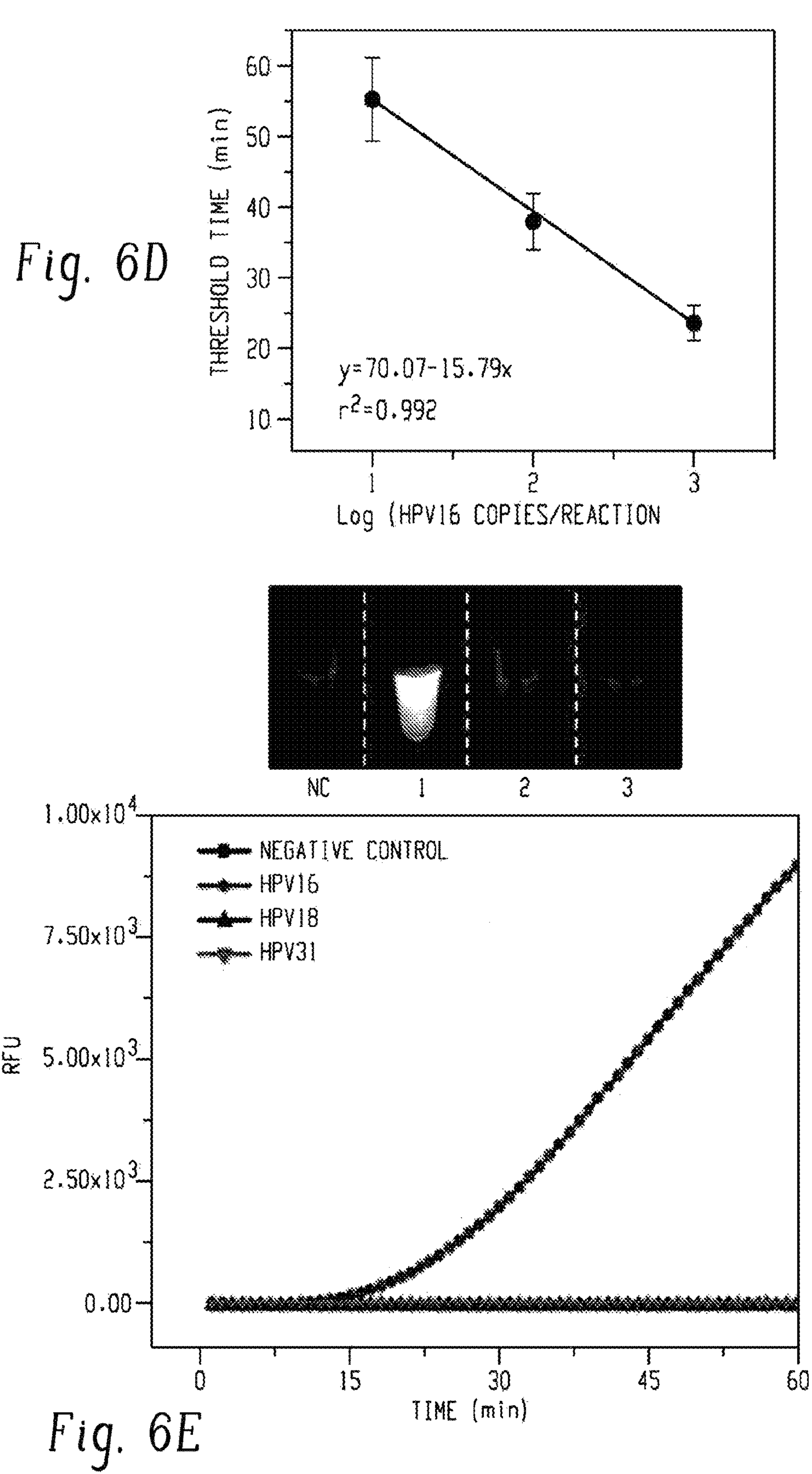
Figure 7A:
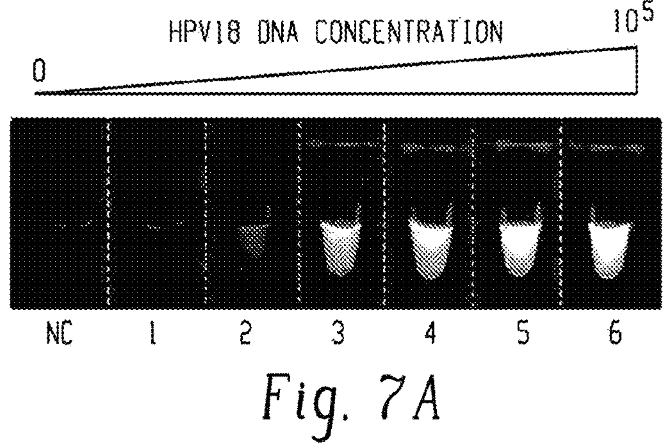
FIG. 7A-D illustrates HPV 18 DNA detection by RPA-CRISPR/Cas12a in an aqueous two-phase system. 7A-D show ten-fold serial diluted HPV 18 DNA (0, 1, 10, $10^2$, $10^3$, $10^4$, $10^5$ copies/reaction) was added into a 20 μL RPA reaction bottom phase (with 10% sucrose and specific primers) in the aqueous two-phase system and incubated at 37° C. for 1 hour. 7A shows a fluorescent image after reaction taken by a ChemiDoc™ MP Imaging System. 7B shows a fluorescent image taken by camera under blue light. 7C shows a real-time fluorescent signal collected by PCR machine. 7D shows the linear relationship between the threshold time and HPV18 concentration. (n=3).
Figure 7B:
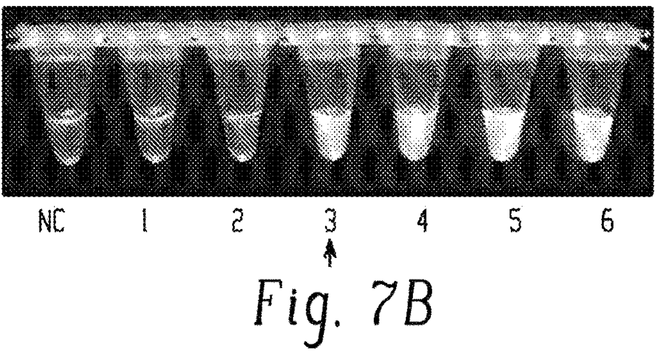
Figure 7C:
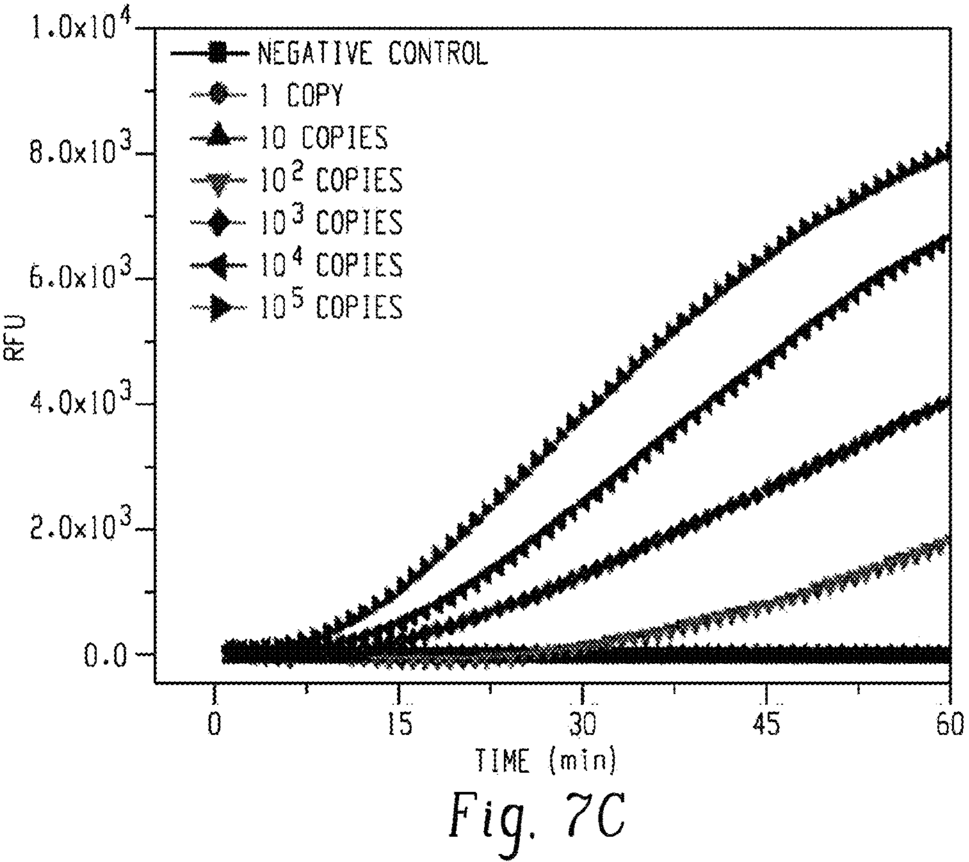
Figure 7D:
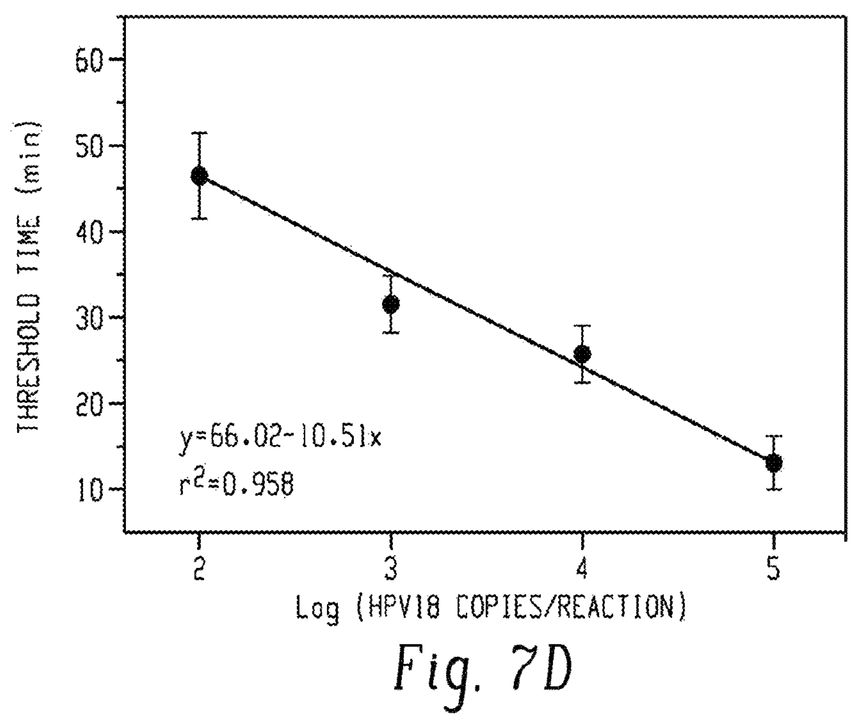
Figure 8:
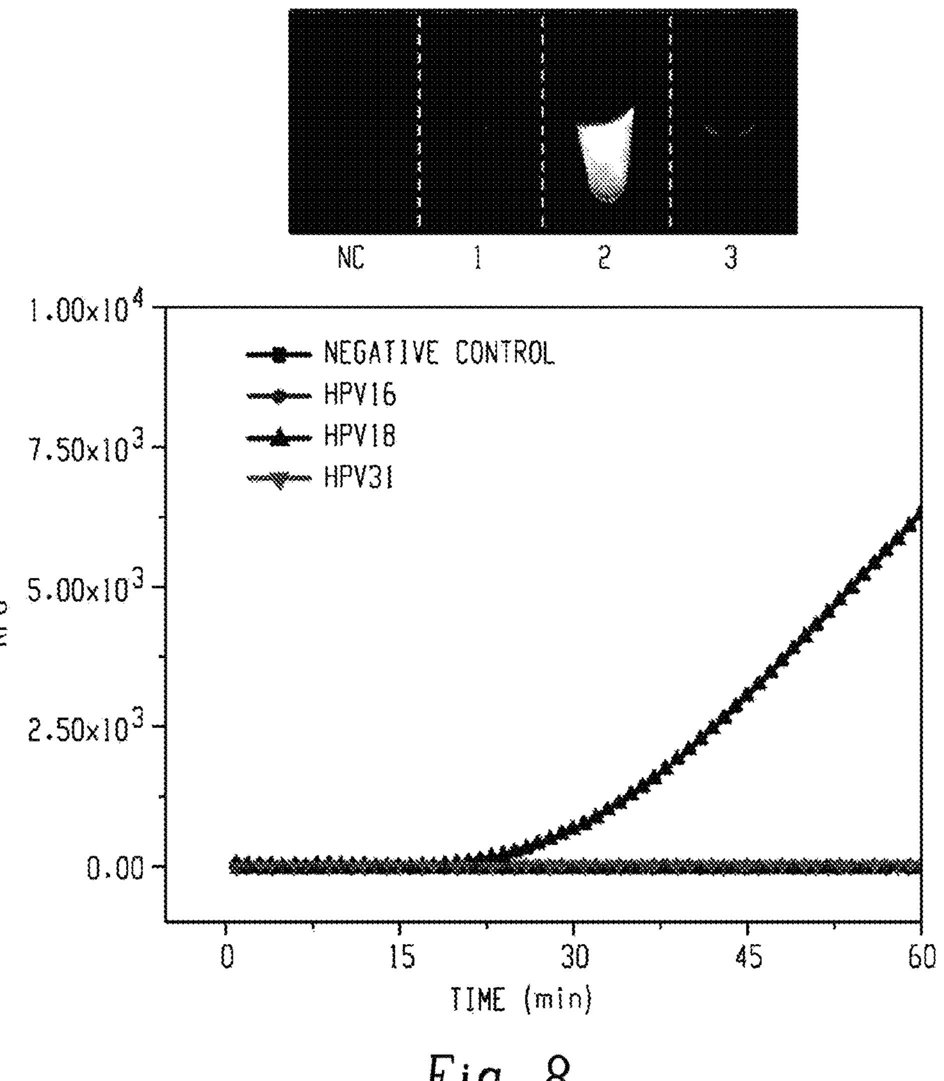
FIG. 8 illustrates the selective detection of HPV18 DNA by RPA-CRISPR/Cas12a in aqueous two-phase system. $10^4$ copies HPV 16, 18 and 31 DNA was added into a 20 μL RPA reaction a bottom phase (10% sucrose and HPV18 RPA primers) in the aqueous two-phase system and incubated at 37° C. for 1 hour, respectively. A fluorescent image on the top was taken by a ChemiDoc™ MP Imaging System. The real-time fluorescent signal curve was collected by a PCR machine.
Figures 10A, 10B, 10C, 10D, 10E:
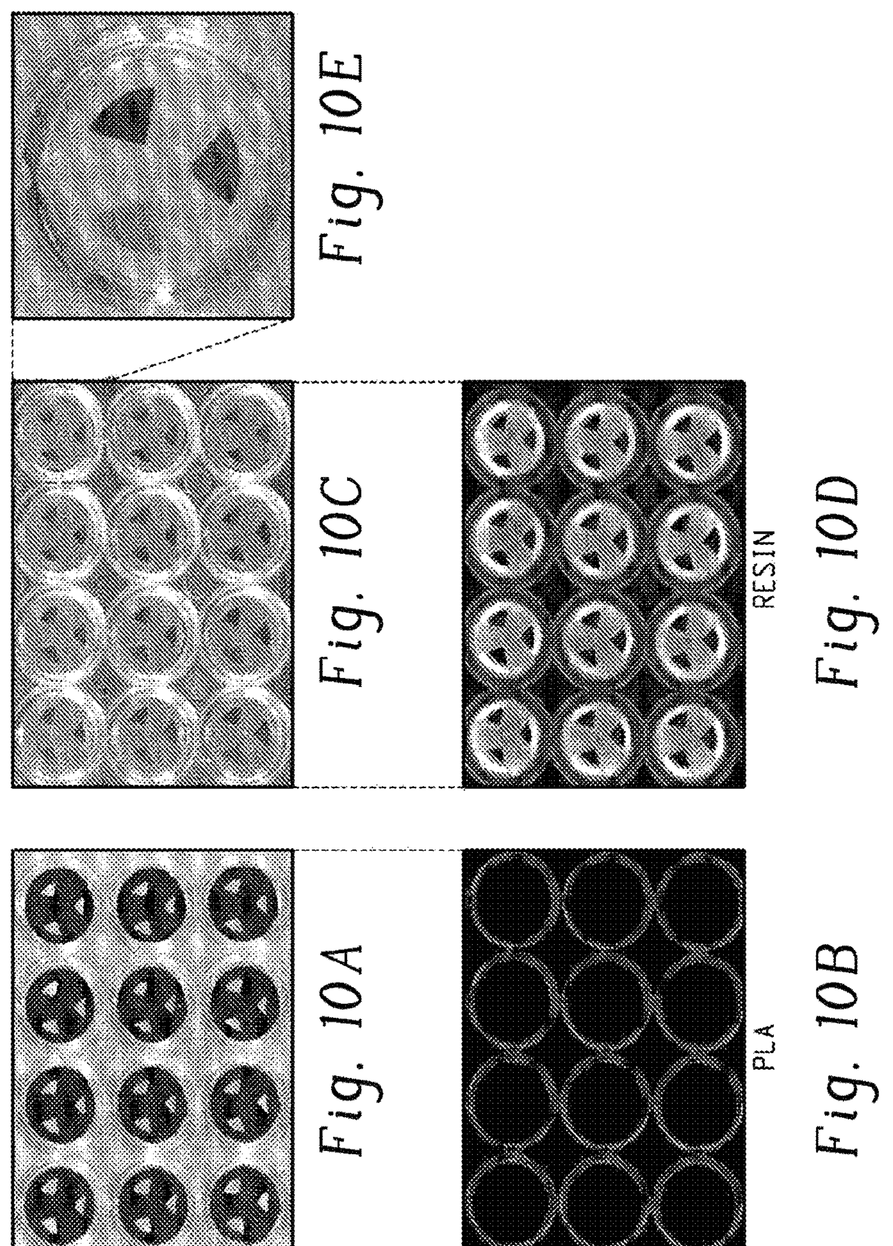
FIG. 10A-E illustrates a 3D-printed device in a microplate. 10A-B show a 3D-printed device using PLA material (3A: bright view, 3B: Fluorescent image taken by a ChemiDoc™ MP Imaging System). 10C-D show a 3D-printed device using a resin material (A: bright view, B: fluorescent image taken by a ChemiDoc™ MP Imaging System). 10E shows different dyes added into the top phase in different chambers respectively and incubated at 37° C. for 1 h.

The quantitative detection of pathogens is crucial for the quantitative estimation of health risks and the classification of disease severity. In previous studies, target amplification was firstly achieved by RPA reaction and followed by a detection process based on the activated CRISPR/Cas12a. Firstly, ten-fold serial diluted HPV 16 and 18 DNA were detected using previous two-step detection method. As shown in FIG. 4A-B, 10 copies and higher concentration of HPV16 DNA can be detected by this method with obvious fluorescent signal difference compared with the negative control. However, the real-time fluorescent signal and the threshold time is similar with each other from $10^2$ copies HPV16 DNA to $10^4$ copies (FIG. 4C-D), which indicated that the quantitative detection is a big challenge using separated target amplification and detection processes. The detection results of ten-fold serial diluted HPV18 DNA also confirmed this conclusion (FIG. 5). In comparison, the RPA-CRISPR/Cas12a in aqueous two-phase system could also detect 10 copies HPV 16 (FIG. 6A-C) and 100 copies HPV18 (FIG. 7A-C) and the obvious fluorescent signal can be clearly recognized by naked eyes under blue light. A good linear relationship between the threshold time and HPV 16/18 concentration was achieved (FIG. 6D and FIG. 7D). The results indicated that quantitative detection can be realized in this aqueous two-phase system through dynamic diffusion, even though the target amplification and detection processes were in different phases. With the help of specific RPA primers during the RPA reaction and specific crRNA targeting, the L1 gene within HPV16 or HPV18 in CRISPR/Cas12a buffer, selectivity was also realized using RPA-CRISPR/Cas12a in an aqueous two-phase system (FIG. 6E and FIG. 8).

Example 5: Human Clinical Swab Sample Detection

Figure 9A:
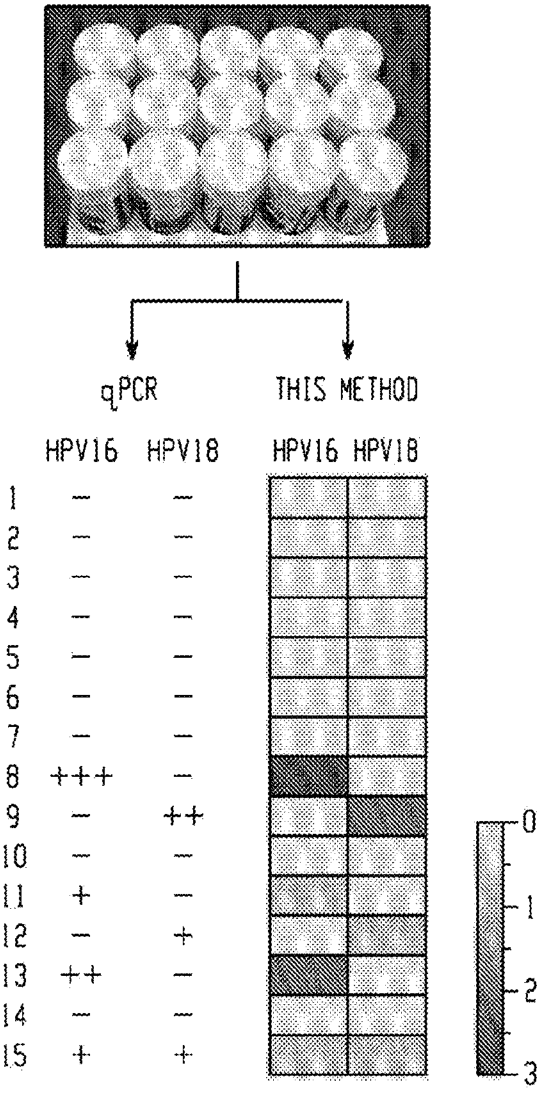
Figure 9B:
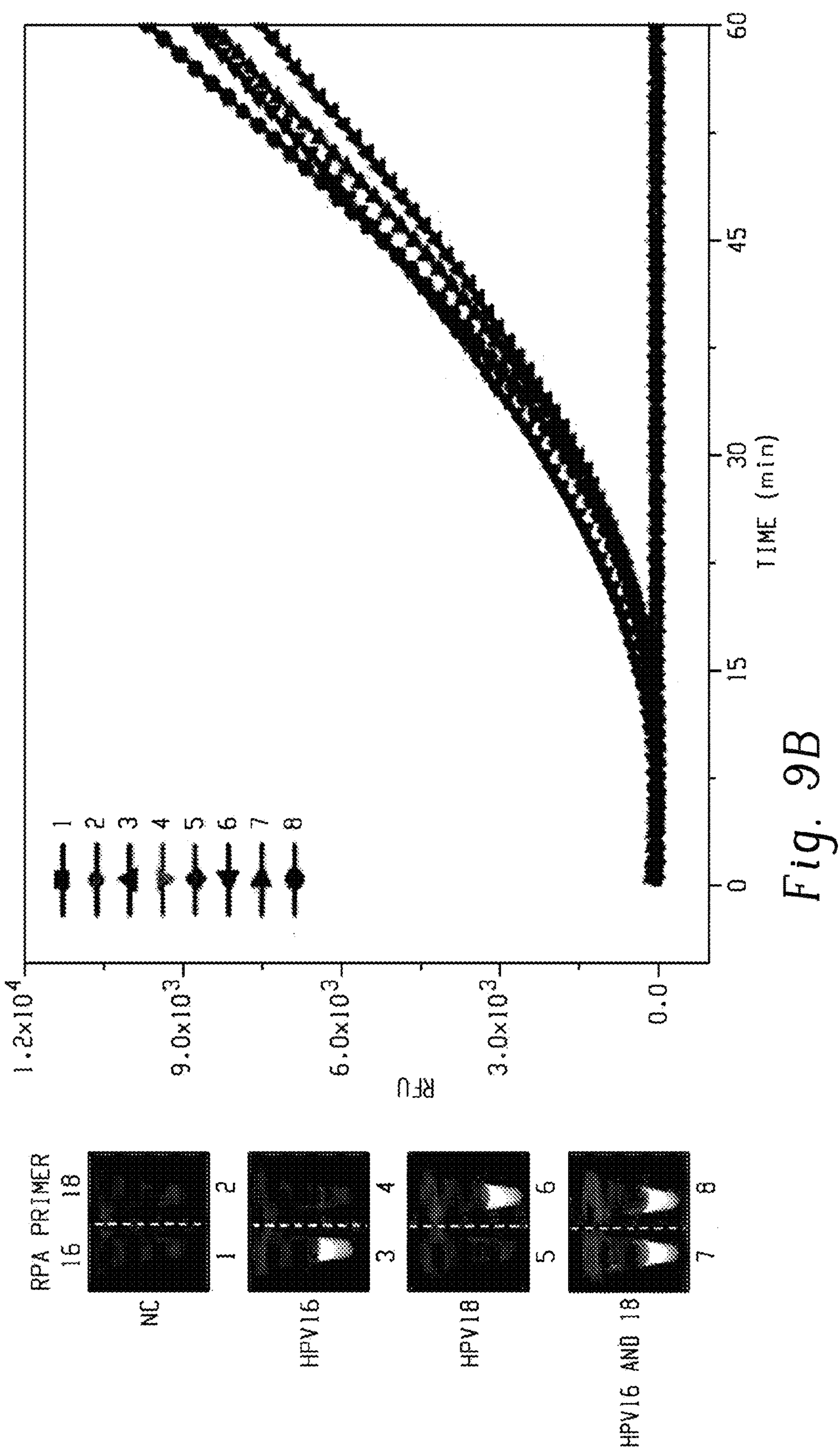

HPV causes almost 99% cervical cancers and some other cancers including vagina, oropharynx and vulva. Recent research confirmed that HPV testing could detect cervical neoplasia earlier than cytology test for cervical cancer screening. Therefore, we evaluated the utility of developed aqueous two-phase detection system for HPV detection from human clinical swab samples. The DNA extracted from clinical samples was detected by developed RPA-CRISPR/Cas12a quantitative detection in aqueous two-phase system and traditional qPCR method, respectively. The HPV level has been classified for four degrees based on the threshold time. Within one hour, the HPV16 and HPV18 can be accurately identified by developed method, which 100% agreement with traditional qPCR method (FIG. 9A). Additionally, we added the HPV DNA into 20 μL RPA reaction solution (10% sucrose) with both HPV16 and HPV18 primers as the bottom phase. And 10 μL CRISPR/Cas12a reaction solution with specific crRNA was the top phase. As shown in FIG. 9B, the target could be correctly identified, which showed the potential for high-throughput multiplex with 3D-printed device in 96-well microplate. PLA material was used for 3D printing to avoid background fluorescence (FIG. 10A-D). The top phase solution would not diffuse to other detection channels after incubated at 37° C. for 1 h (FIG. 10E), because the RPA bottom phase (10% sucrose) covering the well bottom and ⅓ of chamber could separate the CRISPR/Cas12a reaction in the respective chamber. During this detection, HPV DNA extracted from clinical sample 1, 11, 12 and 15 was added into the RPA bottom phase (10% sucrose) with both HPV16 and HPV18 primers. CRISPR/Cas12a reaction solution with/without specific crRNA was added into different chamber as the top phase (FIG. 9D). As shown in FIG. 9E, the target HPV DNA from clinical samples could be successfully identified after incubation at 37° C. for 1 h, which indicated that this high-throughput multiplex system could in principle selectively detect various DNA biomarkers with high sensitivity. All above results demonstrate a novel, high-throughput platform for CRISPR-based multiplex molecular diagnostics.

Example 6: HPV Spiked Human Plasma Sample Detection without Pre-Treatment

Figures 11A, 11B, 11C:
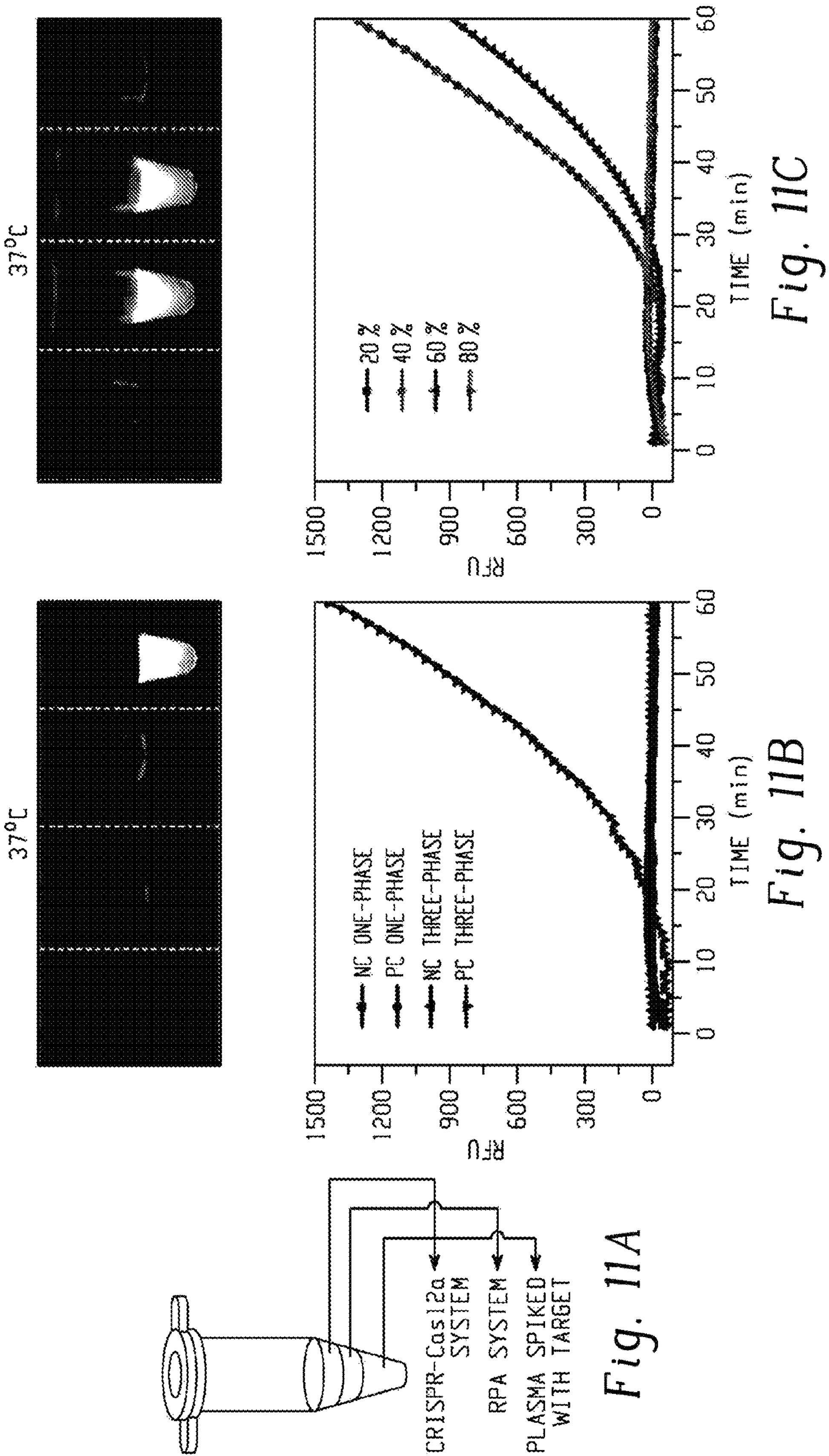
FIG. 11A-F illustrates a dynamic multiphase system for plasma sample detection without pre-treatment. 11A shows an aqueous three-phase system for plasma sample detection by RPA-CRISPR/Cas12a system. 11B illustrates plasma-RPA-CRISPR/Cas12a aqueous three-phase detection. 11C shows optimization of sucrose concentration in the bottom plasma phase. 11D shows an aqueous two-phase system for plasma sample detection by LAMP or qPCR method. 11E shows plasma-LAMP aqueous two-phase detection. 11F shows plasma-qPCR aqueous two-phase detection.
Figures 11D, 11E, 11F:
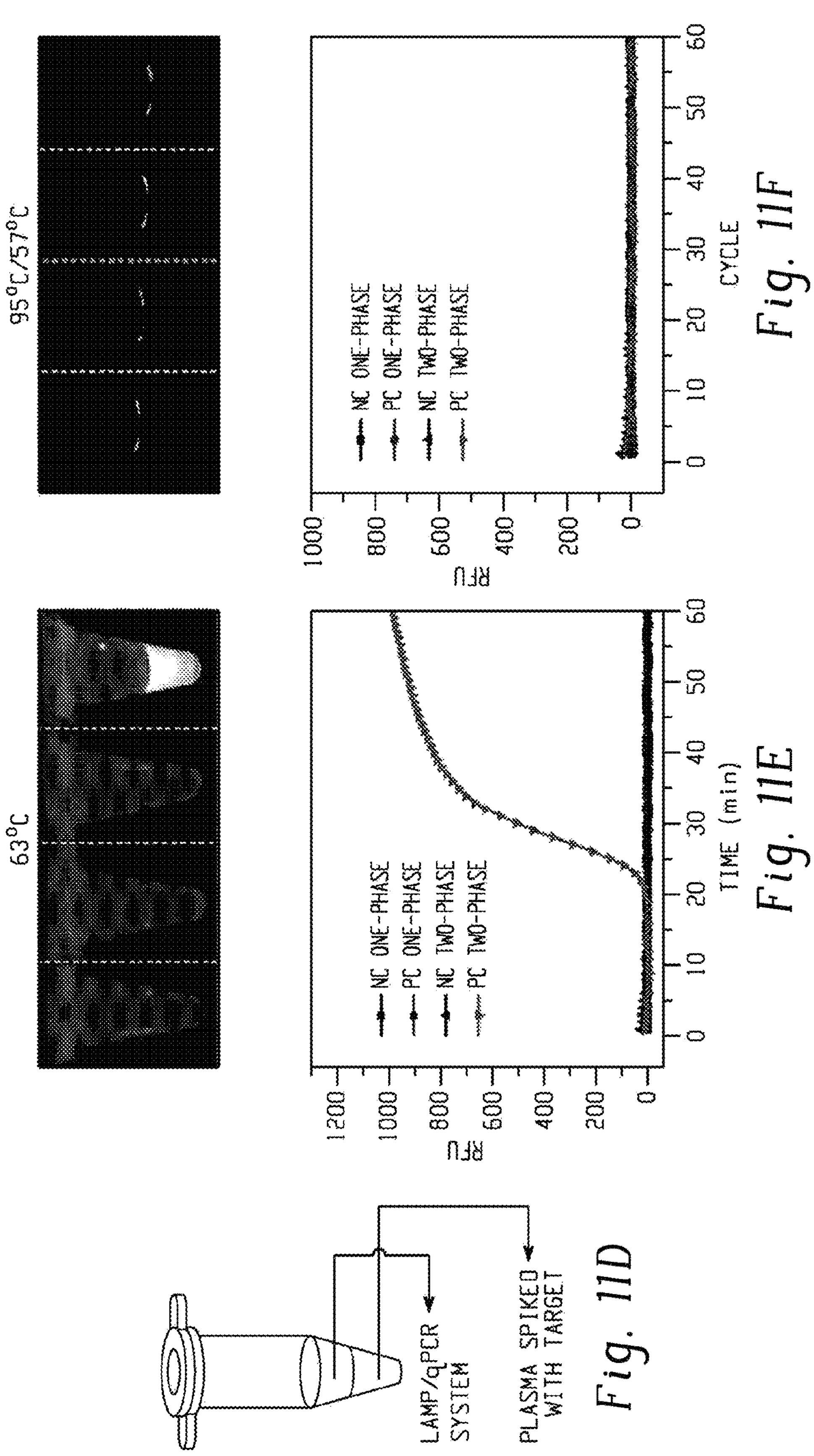

Inhibitors including immunoglobulin G, haemoglobin and lactoferrin in human plasma samples will inhibit target nucleic acids amplification through RPA, LAMP or PCR methods. Therefore, target DNA should be purified from the plasma samples before amplification, which is complicated and may induce cross contamination. To overcome this challenge, the developed dynamic multiphase system was utilized to directly detect target DNA in human plasma samples using RPA-CRISPR/Cas12a method. As shown in FIG. 11A, 10 μL plasma spiked with $10^4$ copies HPV16 DNA with 40% sucrose was added into the PCR tube as the bottom phase. A 20 μL RPA reaction with 10% sucrose was the middle phase. And 10 μL CRISPR/Cas12a reaction solution was added as the top phase (FIG. 11A). An obvious fluorescent signal can be recognized in aqueous three-phase system after 1 h incubation at 37° C., but no fluorescent signal could be recognized in the one-phase system, which confirmed that the inhibitors in the human plasma will not influence RPA-CRISPR/Cas12a detection in aqueous three-phase system (FIG. 11B). The sucrose concentration can be optimized to make sure the inhibitors were locked in the bottom phase, but small size target DNA can dynamically diffuse to the middle and top phase to complete the detection (FIG. 11C). Additionally, we further evaluated the capability of aqueous two-phase system for directly detecting target DNA in human plasma samples using LAMP and qPCR method. As shown in FIG. 11D, 10 μL plasma spiked with $10^4$ copies HPV16 DNA with 40% sucrose was the added into the PCR tube as the bottom phase. 20 μL LAMP or PCR solution was added into the tube as the top phase. An obvious fluorescent signal after LAMP reaction can be recognized after 1 h incubation at 63° C. using aqueous two-phase system (FIG. 11E) but no signal can be collected using qPCR method, which indicated that the inhibitors in human plasma perhaps diffuse to the top phase under high temperature. The results demonstrate a novel platform for the direct detection of target DNA in human plasma samples using dynamic multiphase system.

Figures 12A, 12B:
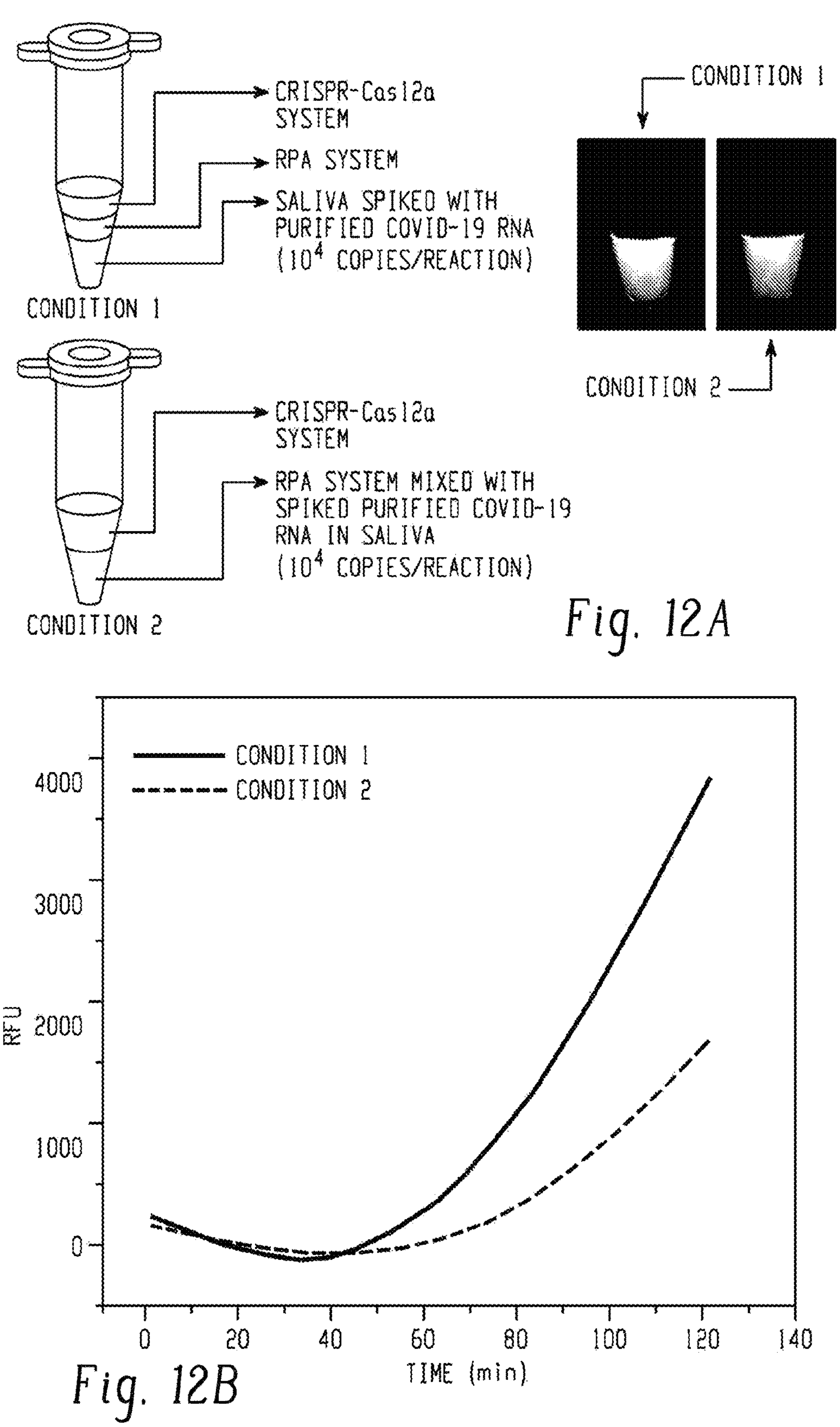
FIG. 12A-B illustrates detection of SARS-CoV-2 RNA spiked in saliva in (Condition 1) three-phase DAMR system and (Condition 1) two-phase DAMR system. 12A illustrates Conditions 1 and 2 and the fluorescence produced by Conditions 1 and 2. 12B is a graphical representation of the fluorescence produced by Conditions 1 and 2. Both DAMR systems 1 and 2 can directly detect SARS-CoV-2 RNA in saliva samples, and the three-phase DAMR system showed stronger fluorescence signals.
Figures 13A, 13B:
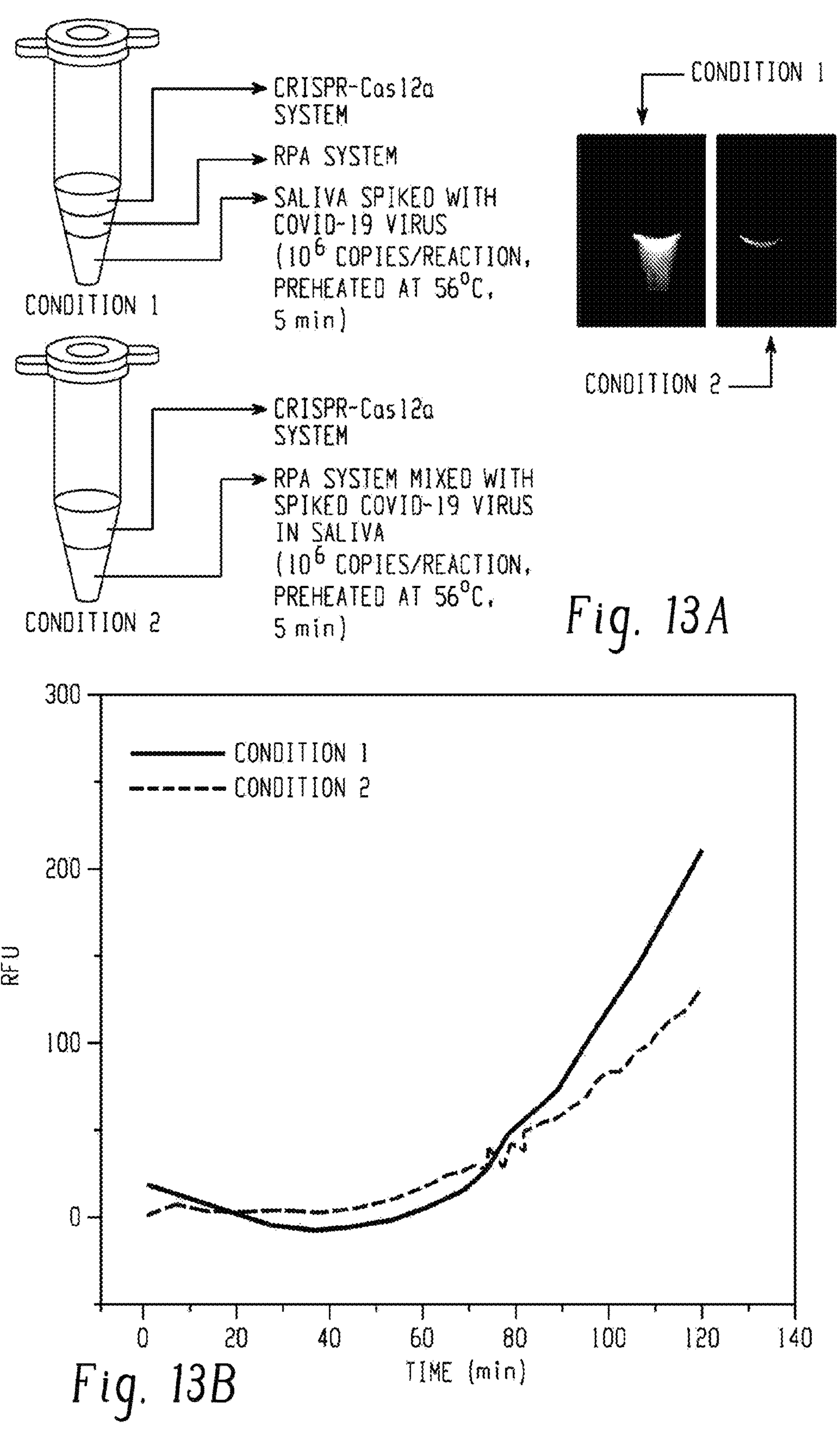
FIG. 13A-B illustrates detection of SARS-CoV-2 virus spiked in saliva in (Condition 1) three-phase DAMR system and (Condition 2) two-phase DAMR system. The spiked samples are preheated at 56° C. for 5 min. 13A illustrates Conditions 1 and 2 and the fluorescence produced by Conditions 1 and 2. 13B is a graphical representation of the fluorescence produced by Conditions 1 and 2. Both DAMR systems can directly detect SARS-CoV-2 virus in saliva samples, and the three-phase DAMR system showed stronger fluorescence signals.
Figures 14A, 14B:
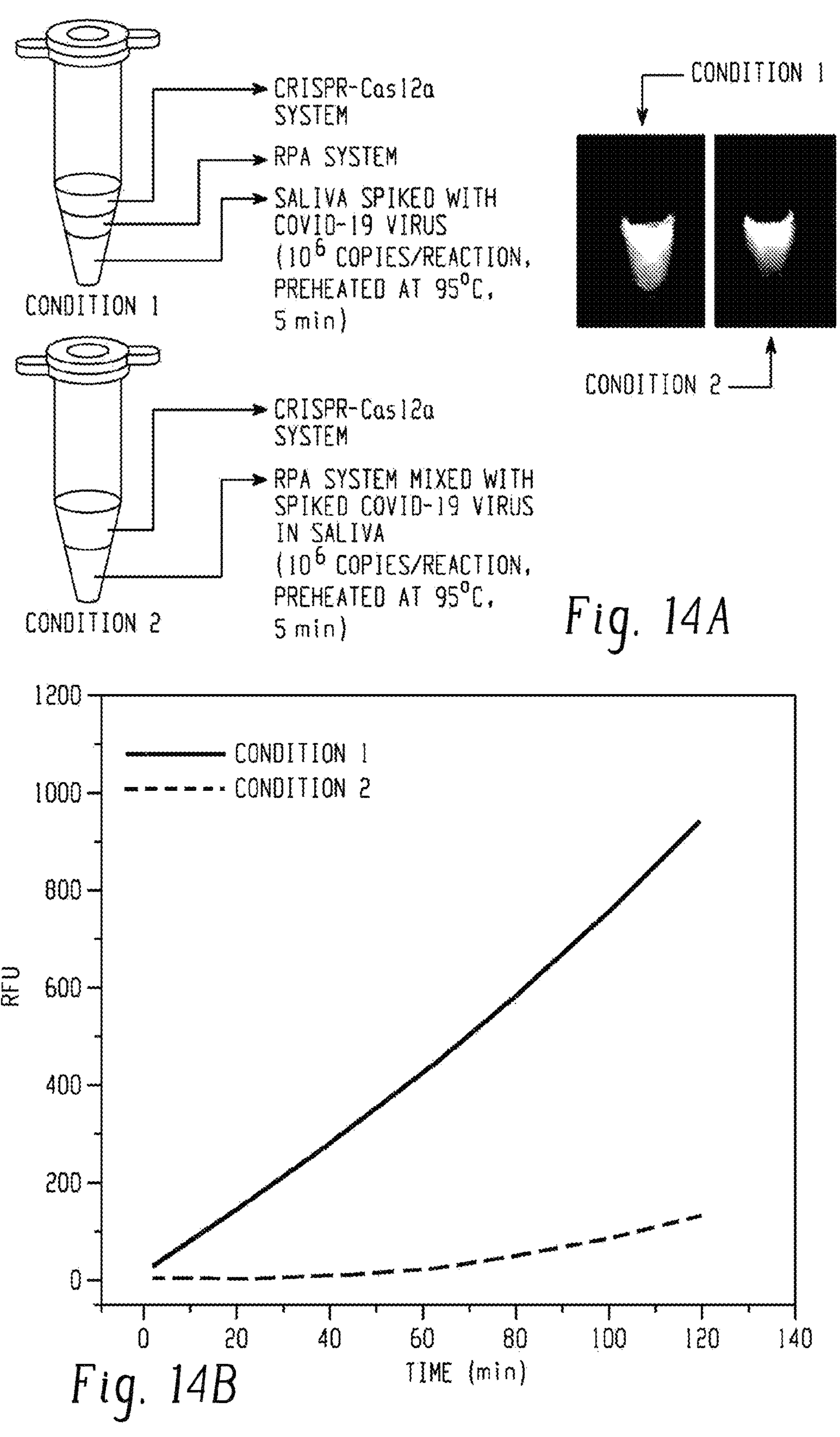
FIG. 14A-B show detection of SARS-CoV-2 virus spiked in saliva in (Conditionl) three-phase DAMR system and (Condition 2) two-phase DAMR system. The spiked samples are preheated at 95° C. for 5 min. 14A illustrates Conditions 1 and 2 and the fluorescence produced by Conditions 1 and 2. 14B is a graphical representation of the fluorescence produced by Conditions 1 and 2. Both DAMR systems can directly detect SARS-CoV-2 virus in saliva samples, and the three-phase DAMR system showed stronger fluorescence signals.

Example 7: Dynamic Aqueous Multiphase Reaction (DAMR) System for SARS-CoV-2 Detection in Saliva As shown in FIG. 12A-C, SARS-CoV-2 RNA spiked in saliva was detected in a (ONE) three-phase DAMR system and (TWO) two-phase DAMR system. Both DAMR systems can directly detect SARS-CoV-2 RNA in saliva samples, and the three-phase DAMR system showed stronger fluorescence signals. As shown in FIG. 13A-C, SARS-CoV-2 RNA spiked in saliva was detected in (ONE) three-phase DAMR system and (TWO) two-phase DAMR system. The spiked samples are preheated at 56° C. for 5 min. Both DAMR systems can directly detect SARS-CoV-2 RNA in saliva samples, and the three-phase DAMR system showed stronger fluorescence signals. As shown in FIG. 14A-C, SARS-CoV-2 virus spiked in saliva in (ONE) three-phase DAMR system and (TWO) two-phase DAMR system. The spiked samples are preheated at 95° C. for 5 min. Both DAMR systems can directly detect SARS-CoV-2 virus in saliva samples, and the three-phase DAMR system showed stronger fluorescence signals. The DAMR system can directly detect SARS-CoV-2 RNA/virus without need for nucleic acid extraction. The detection efficiency of the three-phase DAMR system is higher than those in two-phase DAMR system. Also, heat treatment can improve the detection efficiency.

Discussion

CRISPR/Cas systems have shown remarkable potential for developing next-generation diagnostic biosensing platforms because of their outstanding advantages over traditional molecular diagnosis methods, including their speed, accuracy and sensitivity. However, CRISPR/Cas systems alone sometimes lack the sensitivity to detect low amounts of nucleic acid biomarkers, requiring coupling with isothermal amplification methods to enhance sensitivity. However, the components in CRISPR/Cas buffer partly inhibit RPA, and the nonspecific trans cleavage activity of activated Cas12a will also cleavage target nucleic acids, which requires separation of the amplification and detection processes. In this study, a dynamic multiphase reaction was used to develop a novel, ultrasensitive RPA-CRISPR/Cas12a quantitative detection platform and achieve high-throughput multiplex detection with the help of 3D-printed devices in a 96-well microplate. The target amplification in the RPA reaction can be carried out independently at the beginning, but connected with a CRISPR/Cas system, to generate a fluorescent signal through dynamic diffusion, which finally achieves molecular level target detection.

The density-induced aqueous multiphase system based on sucrose solution described herein is a miscible multiphase system that offers an independent but connected environment through dynamic diffusion. This miscible multiphase system can combine incompatible RPA reaction and CRISPR/Cas together. In the beginning, the amplification of target nucleic acid can be achieved by RNA reaction and then dynamically diffuse to the CRISPR/Cas top phase to Cas12a. The activated trans cleavage activity of Cas12a further cleave the fluorophore quencher (FQ)-labeled ssDNA probe to realized high-efficiency qualitatively or quantitatively detection in one-pot (FIG. 1). The appropriate diffusion rate is crucial to realize the best detection performance, which is related to the sucrose concentration and the volume ratio of different phase (FIG. 3). Under optimal conditions, target detection using RPA-CRISPR/Cas12a quantitative detection in aqueous two-phase system is about 100 times higher than the detection directly mixed RPA and CRISPR/Cas12a, which needs more than 100 times longer time to generate the similar recognizable fluorescent signal.

Cervical cancer is highly related to HPV, particularly high-risk genotype HPV16 and HPV18 which are responsible for almost 70% of all cervical cancer cases. The early and multiplex detection of HPV high-risk genotypes is still an elusive goal for HPV testing and cervical cancer screening. In this developed method, the extracted DNA from clinical samples were first amplified by RPA in the bottom phase and then dynamically diffused to the CRISPR/Cas12a top phase for detection. After coupling with isothermal amplification RPA, attomolar sensitivity was successfully achieved in one-pot aqueous two-phase detection with high-specificity (FIG. 4,5). Compared with conventional qPCR method for HPV testing, the developed method showed 100% agreement with excellent reliability for the detection of high-risk genotype HPV16 and HPV18 in patient samples (FIG. 6). Multiplex detection from a single clinical sample has become increasingly desirable for disease diagnostics. However, it is still a big challenge for POC multiplex biosensing because of the possible cross-reaction, compromised sensitivity and the complexity of bio-matrix. The RPA-CRISPR/Cas12a quantitative detection in aqueous two-phase system has demonstrated the possibility for multiplex detection. Additionally, this novel detection platform also exhibited great potential for high-throughput molecular diagnosis with the help of 3D-printed device in 96-well microplate (FIG. 10).

Circulating HPV DNA in human plasma sample is a prognostic marker of cervical cancer recurrences and metastases. Additionally, the plasma HPV DNA detection is very important for the better understanding the natural history of HPV infection. However, a target amplification method including the RPA method can be inhibited by plasma, which requires sample pre-treatment before amplification. An aqueous multiphase system can restrict inhibitors in the bottom phase, but the small size DNA can dynamically diffuse to the RPA phase can start RPA-CRISPR/Cas12a quantitative detection (FIG. 9). The performance was influenced by the diffusion rate which was related with reaction temperature. Therefore, isothermal amplification methods under low temperature own better performance in aqueous multiphase system when detect real clinical samples without pre-treatment.

Overall, a novel aqueous dynamic multiphase reaction system has been developed to achieve incompatible but correlative reactions in one-pot. State-of-art RPA-CRISPR/Cas12a quantitative detection, the candidate of next-generation diagnostic biosensing platform, has been successfully achieved using an aqueous two-phase system in one-pot with molecular level sensitivity and 100-times higher signal intensity than directly mix all reagents. Combined with a 3D-printed device in a microplate, multiplex high-throughput detection of high-risk genotypes HPV16 and 18 from clinical human swab samples is realized using this developed method with excellent reliability, which 100% agrees with the results from gold-standard qPCR method. The novel, multiplex, high-throughput, quantitative, CRISPR-based detection platform is completely compatible with various nucleic acid biomarkers and shows great potential for POC diagnosis and disease prevention. Additionally, bio-samples such as human plasma samples are compatible with this developed dynamic multiphase reaction system without complicated sample pre-treatment, which addresses the challenge of the inhibitors from real samples and greatly simplifies the detection process.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. An aqueous, miscible, multiphase, one-pot detection system, comprising a first phase comprising a solution comprising a nucleic acid detection system; and a second phase in diffusive communication with the first phase, the second phase comprising a solution having a higher density than the first phase, and a nucleic acid amplification system.

2. The system of claim 1, wherein the solution of the first phase and/or the solution of the second phase is a sucrose solution, a polysucrose solution, a glycerol solution, a sorbitol solution, a copolymerized sucrose and epichlorohydrin solution, a dextran solution, or a combination thereof.

3. The system of claim 1, wherein the nucleic acid amplification system comprises Nucleic Acid Sequence Based Amplification (NASBA), Transcription Mediated Amplification (TMA), Helicase Dependent Amplification (HDA), Recombinase polymerase amplification (RPA), Strand Displacement Amplification (SDA), Loop-mediated Isothermal Amplification (LAMP), Chimera Displacement Reaction (RDC), Isothermal Chimeric Amplification of Nucleic Acids (ICAN), SMart Amplification Process (SMAP), Linear Isothermal Multimerization Amplification (LIMA), Dual-Priming Isothermal Amplification (DAMP), isothermal multiple-self-matching-initiated amplification (IMSA) or Self Extending Amplification (SEA).

4. The system of claim 3, wherein the recombinase polymerase amplification system comprises a single-stranded deoxyribonucleic acid (DNA)-binding protein (SSB), a recombinase, and a strand-displacing polymerase.

5. The system of claim 1, wherein the nucleic acid detection system comprises a Type V clustered regularly interspaced short palindromic repeats (CRISPR)/Cas detection system, a colorimetric detection system, a bioluminescence detection system, or an electrochemical detection system.

6. The system of claim 1, wherein the nucleic acid detection system is a clustered regularly interspaced short palindromic repeats (CRISPR)/Cas detection system comprising a Cas12a endonuclease, a CRISPR ribonucleic acid (crRNA) comprising a complementary sequence to a target sequence, and a single-stranded reporter deoxyribonucleic acid (DNA) comprising a detectable label.

7. The system of claim 1, wherein the volume ratio of the first phase to the second phase is 1:10 to 10:1.

8. The system of claim 1, further comprising a third phase, the third phase comprising a solution having a higher density than the second phase, wherein the third phase is in diffusive contact with the second phase.

9. The system of claim 8, wherein the third phase comprises a nucleic acid preparation system.

10. A multiwell plate and/or a device comprising the system of claim 1.

11. A method of detecting a target nucleic acid in a nucleic acid sample suspected of containing the target nucleic acid, the method comprising providing the system of claim 1, wherein the first phase comprises a detectable label; and amplifying the target nucleic acid in the second phase for a time sufficient to provide an amplified target nucleic acid and to allow the amplified target nucleic acid to diffuse to the first phase, wherein diffusion of the amplified target nucleic acid to the first phase activates the nucleic acid detection system and turns on the detectable label providing detection of the target nucleic acid in the nucleic acid sample.

12. The method of claim 11, wherein the solution of the second phase is a sucrose solution, a glycerol solution, or a polysucrose solution.

13. The method of claim 11, wherein the nucleic acid amplification system comprises Nucleic Acid Sequence Based Amplification (NASBA), Transcription Mediated Amplification (TMA), Helicase Dependent Amplification (HDA), Recombinase polymerase amplification (RPA), Strand Displacement Amplification (SDA), Loop-mediated Isothermal Amplification (LAMP), Chimera Displacement Reaction (RDC), Isothermal Chimeric Amplification of Nucleic Acids (ICAN), SMart Amplification Process (SMAP), Linear Isothermal Multimerization Amplification (LIMA), Dual-Priming Isothermal Amplification (DAMP), isothermal multiple-self-matching-initiated amplification (IMSA), or Self Extending Amplification (SEA).

14. The method of claim 13, wherein the recombinase polymerase amplification system comprises a single-stranded deoxyribonucleic acid (DNA)-binding protein (SSB), a recombinase, and a strand-displacing polymerase.

15. The method of claim 11, wherein the nucleic acid detection system comprises a Type V clustered regularly interspaced short palindromic repeats (CRISPR)/Cas detection system, a colorimetric detection system, a bioluminescence detection system, or an electrochemical detection system.

16. The method of claim 11, wherein the nucleic acid detection system is a clustered regularly interspaced short palindromic repeats (CRISPR)/Cas detection system comprising a Cas12a endonuclease, a CRISPR ribonucleic acid (crRNA) comprising a complementary sequence to a target sequence, and a single-stranded reporter deoxyribonucleic acid (DNA) comprising a detectable label.

17. The method of claim 11, further comprising providing a third phase, the third phase comprising a solution having a higher density than the second phase, wherein the third phase is in diffusive contact with the second phase, and wherein the third phase comprises an unpurified sample comprising the nucleic acid sample, wherein the nucleic acid sample is cell-free nucleic acids and diffuses from the third phase to the second phase.

18. The method of claim 17, wherein the unpurified sample is a blood sample, a saliva sample, or a tissue sample.

19. The method of claim 11, wherein the target nucleic acid is a pathogen deoxyribonucleic acid (DNA), a pathogen ribonucleic acid (RNA), or a biomarker of disease.

20. The method of claim 11, wherein amplifying is done at a temperature of 30° C. to 65° C.

* * * * *